United States Patent
McBride et al.

(10) Patent No.: US 12,226,468 B2
(45) Date of Patent: Feb. 18, 2025

(54) IMMUNOREACTIVE PEPTIDES

(71) Applicant: Research Development Foundation, Carson City, NV (US)

(72) Inventors: Jere McBride, Galveston, TX (US); David Walker, Galveston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 18/754,918

(22) Filed: Jun. 26, 2024

(65) Prior Publication Data

US 2024/0424075 A1  Dec. 26, 2024

Related U.S. Application Data

(60) Provisional application No. 63/510,310, filed on Jun. 26, 2023.

(51) Int. Cl.
| | | |
|---|---|---|
| A61K 39/02 | (2006.01) | |
| A61K 39/39 | (2006.01) | |
| C07K 14/29 | (2006.01) | |
| G01N 33/569 | (2006.01) | |
| A61K 39/00 | (2006.01) | |

(52) U.S. Cl.
CPC ......... *A61K 39/0233* (2013.01); *A61K 39/39* (2013.01); *C07K 14/29* (2013.01); *G01N 33/56911* (2013.01); *A61K 2039/55566* (2013.01); *C07K 2319/40* (2013.01); *C07K 2319/41* (2013.01); *C07K 2319/42* (2013.01); *G01N 2333/29* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 6,136,610 | A  | 10/2000 | Polito et al. |
| 6,685,885 | B2 | 2/2004  | Nolte et al. |
| 7,344,893 | B2 | 3/2008  | Kirkegaard et al. |
| 7,371,582 | B2 | 5/2008  | Nahm et al. |
| 7,405,831 | B2 | 7/2008  | Nolte et al. |
| 7,552,282 | B1 | 6/2009  | Bermingham et al. |
| 7,659,968 | B2 | 2/2010  | Wang et al. |
| 7,663,092 | B2 | 2/2010  | Nolte et al. |
| 8,980,288 | B2 | 3/2015  | Diehl et al. |
| 9,545,439 | B2 | 1/2017  | Diehl et al. |
| 9,662,385 | B2 | 5/2017  | Dominowski et al. |
| 10,001,699 | B2 | 6/2018 | Orihara et al. |
| 10,117,921 | B2 | 11/2018 | Dominowski et al. |
| 11,046,734 | B2 | 6/2021 | McBride et al. |
| 11,780,892 | B2 | 10/2023 | McBride et al. |
| 2002/0177178 | A1 | 11/2002 | Lawton et al. |
| 2005/0047972 | A1 | 3/2005 | Lauks et al. |
| 2005/0065463 | A1 | 3/2005 | Tobinaga et al. |
| 2005/0250141 | A1 | 11/2005 | Lambert et al. |
| 2006/0234322 | A1 | 10/2006 | Krah, III et al. |
| 2009/0005535 | A1 | 1/2009 | Kadzimirzs et al. |
| 2010/0273194 | A1 | 10/2010 | McBride et al. |
| 2010/0330091 | A1 | 12/2010 | McBride et al. |
| 2012/0219972 | A1 | 8/2012 | Thomas et al. |
| 2019/0038737 | A1 | 2/2019 | Dominowski et al. |
| 2020/0026178 | A1 | 1/2020 | Jindal et al. |
| 2020/0031877 | A1 | 1/2020 | McBride et al. |
| 2020/0133111 | A1 | 4/2020 | Liu et al. |
| 2021/0239695 | A1 | 8/2021 | McBride et al. |

FOREIGN PATENT DOCUMENTS

| | | |
|---|---|---|
| EP | 2433646 | 3/2012 |
| TW | 201921086 | 6/2019 |
| TW | 202008073 | 2/2020 |
| TW | 202026770 | 7/2020 |
| WO | WO1998/042740 | 10/1998 |
| WO | WO2000/000615 | 1/2000 |
| WO | WO2002/057794 | 7/2002 |
| WO | WO2005/087803 | 9/2005 |
| WO | WO2006/107924 | 10/2006 |
| WO | WO2006/138509 | 12/2006 |
| WO | WO2008/043000 | 4/2008 |
| WO | WO2009/034575 | 3/2009 |
| WO | WO 2011/125015 | 10/2011 |

OTHER PUBLICATIONS

Ca'rdenas et al., « Enzyme-Linked Immunosorbent Assay with Conserved Immunoreactive Glycoproteins gp36 and gp19 Has Enhanced Sensitivity and Provides Species-Specific Immunodiagnosis of *Ehrlichia* canis, Infection », *Clin. Vacc. Immunol.* 14: 123-128, 2007.

Calabro et al., "The adjuvant effect of MF59 is due to the oil-in-water emulsion formulation, none of the individual components induce a comparable adjuvant effect", *Vaccine*, 31: 3363-3369, 2013.

Carpino et al., « Rapid, Continuous Solution-Phase Peptide Synthesis : Application to Peptides of Pharmaceutical Interest », *Org. Proc. Res. Dev.*, 7(1)28-37, 2003.

Didierlaurent, et al., « Enhancement of adaptive immunity by the human vaccine adjubant AS01 depends on activated dentritic cells », *J. Immunol.* 193(4):1920-1930, 2014.

Doyle et al., « Differentially Expressed and Secreted Major Immunoreactive Protein Orthologs of *Ehrlichia canis* and *E. chaffeensis* Elicit Early Antibody Responses to Epitopes on Glycosylated Tandem Repeats », *Infection and Immunity*, 74(1) :711-720, 2006.

Dumler et al., "Ehrlichioses in humans: epidemiology, clinical presentation, diagnosis, and treatment," *Clin. Infect. Dis.*, 45:S45-S51, 2007.

Feng and Walker, "Mechanisms of immunity to Ehrlichia muris: a model of monocytotropic ehrlichiosis," *Infect. Immun.*, 72:966-971, 2004.

Fishbein et al., "Human ehrlichiosis in the United States, 1985 to 1990," AnnInternMed 120:736-743, 1994.

He et al., "Vaxign: the first web-based vaccine design program for reverse vaccinology and applications for vaccine development," J Biomed Biotechnol 2010:297505, 2010.

(Continued)

*Primary Examiner* — Oluwatosin A Ogunbiyi
(74) *Attorney, Agent, or Firm* — Parker Highlander PLLC

(57) ABSTRACT

Immunoreactive engineered polypeptides are provided. The engineered polypeptides can be used to diagnose or induce an immune response against *E. chaffeensis* or *E. canis*.

29 Claims, 3 Drawing Sheets

Specification includes a Sequence Listing.

(56) References Cited

OTHER PUBLICATIONS

Kuriakose et al., "*Ehrlichia chaffeensis* transcriptome in mammalian and arthropod hosts reveals differential gene expression and post transcriptional regulation," PLoS One 6:e24136, 2011.

Kuriakose et al., "Molecular basis of antibody mediated immunity against *Ehrlichia chaffeensis* involves species-specific linear epitopes in tandem repeat proteins," Microbes Infect 14:1054-1063, 2012.

Li and Winslow, "Survival, replication, and antibody susceptibility of *Ehrlichia chaffeensis* outside of host cells," InfectImmun 71:4229-4237, 2003.

Li et al., "Outer membrane protein-specific monoclonal antibodies protect SCID mice from fatal infection by the obligate intracellular bacterial pathogen *Ehrlichia chaffeensis*," JImmunol 166:1855-1862, 2001.

Li et al., "Antibodies highly effective in SCID mice during infection by the intracellular bacterium *Ehrlichia chaffeensis* are of picomolar affinity and exhibit preferential epitope and isotype utilization," JImmunol 169:1419-1425, 2002.

Lin et al., "Global proteomic analysis of two tick-borne emerging zoonotic agents: *Anaplasma phagocytophilum* and *Ehrlichia chaffeensis*," Front Microbiol 2:24, 2011.

Lou et al., "Major Species-Specific Antibody Epitopes of the Ehrlichia chaffeensis p120 and E-canis p140 Orthologs in Surface-Exposed Tandem Repeat Regions", Clinical and Vaccine Immun., 16(7), 982-990, 2009.

Magnan et al., "High-throughput prediction of protein antigenicity using protein microarray data," Bioinformatics 26:2936-2943, 2010.

McBride and Walker, "Progress and obstacles in vaccine development for the ehrlichioses," Expert Rev Vaccines 9:1071-1082, 2010.

Mizuno et al., "From Peptides to Peptidomimetrics: A strategy Based on the Structural Features of Cyclopropane", Chemistry. 23(58):14394-14409, Oct. 17, 2017.

Nandi et al., "CD4 T-cell epitopes associated with protective immunity induced following vaccination of mice with an ehrlichial variable outer membrane protein," InfectImmun 75:5453-5459., 2007.

Olano et al., "Human monocytotropic ehrlichiosis, Missouri," EmergInfectDis 9:1579-1586, 2003.

Paparone et al., Ehrlichiosis with pancytopenia and ARDS. New Jersey Med 92:381-385, 1995.

Paterson et al., "Persisten luminescence strontium aluminate nanoparticles as reporters in lateral flow assays", Anal Chem. 86(19):9481-8, Oct. 7, 2014.

Racine et al., "IgM production by bone marrow plasmablasts contributes to long-term protection against intracellular bacterial infection," J Immunol 186:1011-1021, 2011.

Sotomay et al., "Animal model of fatal human monocytotropic ehrlichiosis," AmJPath 158:757-769, 2001.

Stuen et al., "Lambs Immunized with an Inactivated Variant of Anaplasma Phagocytophilum," *Acta Vet Scand.*, 57:40, 2015.

Tollersrud et al., "*Staphylococcus aureus* Capsular Polysaccharide Type 5 Conjugate and Whole Cell Vaccines Stimulate Antibody Responses in Cattle," *Vaccine*, 19:3896-3903, 2001.

Vega et al., "Anaplasma Marginale Field Challenge: Protection by an Inactivated Immunogen that Shares Partial Sequence of Msp1alpha Variable Region with the Challenge Strain," *Vaccine*, 25:519-525, 2007.

Walker and Dumler, "Human monocytic and granulocytic ehrlichioses. Discovery and diagnosis of emerging tick-borne infections and the critical role of the pathologist," [Review] [50 refs]. Archives of Pathology & Laboratory Medicine 121:785-791, 1997.

Walker et al., "Ehrlichia chaffeensis: a prevalent, life-threatening, emerging pathogen," Trans Am Clin Climatol Assoc 115:375-382; discussion 382-374, 2004.

Winslow et al., "Infection of the laboratory mouse with the intracellular pathogen *Ehrlichia chaffeensis*," InfectImmun 66:3892-3899, 1998.

Winslow et al., "*Antibody-Mediated Elimination of the Obligate Intracellular Bacterial Pathogen Ehrlichia Chaffeensis During Active Infection,*" Infect. Immun., 68:2187-2195, 2000.

Winslow et al., "Mechanisms of Humoral Immunity During Ehrlichia Chaffeensis Infection," Ann. NY Acad. Sci., 990:435-443, 2003.

Yager et al., "*Essential Role for Humoral Immunity During Ehrlichia Infection in Immunocompetent Mice,*" Infect. Immun., 73:8009-8016, 2005.

International Search Report and Written Opinion for PCT/US2024/035561 issued Sep. 19, 2024, 11 pages.

SEQUENCE LISTING

```
Sequence total quantity: 8
SEQ ID NO: 1            moltype = AA  length = 177
FEATURE                 Location/Qualifiers
source                  1..177
                        mol_type = protein
                        organism = synthetic construct
SEQUENCE: 1
TEDSVSAPAT EDSVSAPATE DSVSAPATED SVSAPATEDS VSAPATEDSV SAPAGGGSYN    60
HNTGLLDLDS DILNMLYSYN HNTGLLDLDS DILNMLYSYN HNTGLLDLDS DILNMLYGGG   120
SKEESTPEVK AEDLQPAVDS KEESTPEVKA EDLQPAVDSK EESTPEVKAE DLQPAVD      177

SEQ ID NO: 2            moltype = AA  length = 81
FEATURE                 Location/Qualifiers
source                  1..81
                        mol_type = protein
                        organism = synthetic construct
SEQUENCE: 2
SYNHNTGLLD LDSDILNMLY SYNHNTGLLD LDSDILNMLY GGGSKEESTP EVKAEDLQPA    60
VDSKEESTPE VKAEDLQPAV D                                              81

SEQ ID NO: 3            moltype = AA  length = 81
FEATURE                 Location/Qualifiers
source                  1..81
                        mol_type = protein
                        organism = synthetic construct
SEQUENCE: 3
SKEESTPEVK AEDLQPAVDS KEESTPEVKA EDLQPAVDGG GSYNHNTGLL DLDSDILNML    60
```

```
YSYNHNTGLL DLDSDILNML Y                                                     81

SEQ ID NO: 4            moltype = AA  length = 61
FEATURE                 Location/Qualifiers
source                  1..61
                        mol_type = protein
                        organism = synthetic construct
SEQUENCE: 4
TEDSVSAPAT EDSVSAPAGG GSYNHNTGLL DLDSDILNML YSYNHNTGLL DLDSDILNML           60
Y                                                                           61

SEQ ID NO: 5            moltype = AA  length = 61
FEATURE                 Location/Qualifiers
source                  1..61
                        mol_type = protein
                        organism = synthetic construct
SEQUENCE: 5
SYNHNTGLLD LDSDILNMLY SYNHNTGLLD LDSDILNMLY GGGTEDSVSA PATEDSVSAP           60
A                                                                           61

SEQ ID NO: 6            moltype = AA  length = 40
FEATURE                 Location/Qualifiers
source                  1..40
                        mol_type = protein
                        organism = synthetic construct
SEQUENCE: 6
SYNHNTGLLD LDSDILNMLY SYNHNTGLLD LDSDILNMLY                                 40

SEQ ID NO: 7            moltype = AA  length = 211
FEATURE                 Location/Qualifiers
source                  1..211
                        mol_type = protein
                        organism = synthetic construct
SEQUENCE: 7
SKVEQEETNP EVLIKDLQDV ASSKVEQEET NPEVLIKDLQ DVASSKVEQE ETNPEVLIKD           60
LQDVASSKVE QEETNPEVLI KDLQDVASGG GDKNKLQDVK DNKPSDVKLP VIKAEDKNKL          120
QDVKDNKPSD VKLPVIKAED KSKLRDVKDN KPSDVKLPVV KAEDKNKLQD VKDNKPSDVK          180
LPVIKAEDKS KLRDVKDNKP SDVKLPVVKA E                                         211

SEQ ID NO: 8            moltype = AA  length = 27
FEATURE                 Location/Qualifiers
source                  1..27
                        mol_type = protein
                        organism = Ehrlichia canis
SEQUENCE: 8
TEDSVSAPAT EDSVSAPATE DSVSAPA                                               27
```

IMMUNOREACTIVE PEPTIDES

This application claims the benefit of U.S. Provisional Patent Application No. 63/510,310, filed Jun. 26, 2023, the entirety of which is incorporated herein by reference.

BACKGROUND

This application contains a Sequence Listing XML, which has been submitted electronically and is hereby incorporated by reference in its entirety. Said XML Sequence Listing, created on Jun. 26, 2024, is named CLFRP0543US.xml and is 8,589 bytes in size.

1. FIELD

The present invention relates generally to the field of molecular biology and medicine. More particularly, it concerns synthetic or recombinant peptides that can be used to diagnose or vaccinate against ehrlichiosis.

2. DESCRIPTION OF RELATED ART

Infectious diseases that affect dogs, cats and other animals having close interactions with humans are important not only from a veterinary standpoint, but also because of the risk to public health. An infectious disease is caused by the presence of organisms such as viruses, bacteria, fungi, or parasites (either animalian or protozoan). Most of these diseases are spread directly from animal to animal, while others require a vector such as a tick or mosquito. Certain infectious diseases are a concern from a public health standpoint because they are zoonoses (transmittable to humans).

The species of *Ehrlichia* that most commonly infects dogs is *Ehrlichia canis*. *Ehrlichia* infects monocytes in the peripheral blood. Several of the proteins produced by *E. canis* result in an immune response in dogs and can be used for diagnosis of ehrlichiosis (Ca'rdenas et al., 2007).

Ehrlichiosis caused by an *E. chaffeensis* infection in humans presents with flu-like symptoms of fever, chills, headache, and muscle aches. In more severe cases, nausea, loss of appetite, weight loss, abdominal pain, cough, diarrhea and change in mental status may also be observed. Ehrlichiosis in humans is potentially fatal.

In dogs, ehrlichiosis is most often caused by either *E. chaffeensis* or *E. canis* bacteria, and progresses in three phases: an acute phase, a subclinical phase, and a chronic phase. The acute phase normally extends weeks after infection and features symptoms similar to those of human ehrlichiosis, such as fever, lethargy, loss of appetite, shortness of breath, joint pain and stiffness, and may also include more severe symptoms such as anemia, depression, bruising, and enlarged lymph nodes, liver, and spleen. The subclinical phase can persist for years and most often presents no symptoms, although antibodies to *Ehrlichia* antigens may be detectable. The chronic phase of *Ehrlichia* infection generally features recurring symptoms of weight loss, anemia, neurological dysfunction, bleeding, ocular inflammation, leg edema, and fever, and presents a blood profile which often leads to a misdiagnosis of leukemia. An *Ehrlichia* infection that progresses to the chronic stage of disease is often fatal.

The nonspecific symptoms of an *Ehrlichia* infection and their resemblance to mild and severe influenza symptoms makes diagnosis of Ehrlichiosis difficult in humans and dogs. Diagnosis can be further hampered by current laboratory testing procedures for *Ehrlichia* infection which are not point-of-care tests, i.e., the tests are not available in most hospitals, clinics, and physician or veterinarian offices where a patient can receive treatment.

Although advances have been made for the diagnosis of infection by *E. canis*, several disadvantages of using full length proteins remains. For example, not all animals (e.g., dogs) that have been infected with *E. canis* will be seropositive for a single full-length protein, and often testing using multiple individual proteins may be needed for increased confidence in the results. Further producing a full-length protein for testing purposes can be laborious and expensive for clinical diagnostic uses. Clearly, there is a need for new peptides for the diagnosis of and vaccination against *E. canis*.

SUMMARY

The present disclosure overcomes limitations in the prior art by providing non-natural engineered polypeptides (e.g., SEQ ID NO:1, SEQ ID NO:7) that can be used to diagnose *Ehrlichia* infection with superior effectiveness as compared to diagnosis using natural *E. canis* protein. These peptides can also be produced more economically and using a greater variety of laboratory techniques including synthetic approaches, as compared to natural full-length *E. canis* proteins. For example, as shown in the below examples SEQ ID NO:1 and SEQ ID NO:7 were tested for seropositivity against sera taken from multiple dogs who had separately been infected with *Ehrlichia*, and, in contrast to results observed using natural highly immunoreactive polypeptide from *Ehrlichia*, improved seropositivity and increased immunoreactivity was observed. The synthetic proteins provided herein can be used in a variety of diagnostic approaches to detect infection by *E. canis*. Depending on the vaccine used, in some instances the engineered peptides provided herein can be used to distinguish between vaccination against *E. canis* and infection by *E. canis*, which may be useful, e.g., for testing of abandoned or stray dog populations.

It is anticipated that SEQ ID NO:2 contained within SEQ ID NO:1 includes multiple antigenic regions that can contribute to the superior results observed for SEQ ID NO:1. In some aspects, it is anticipated that SEQ ID NO:6 within SEQ ID NO:1 includes an antigenic region that can contribute to the effectiveness of SEQ ID NO:1. The results indicate that SEQ ID NO:1 can be used to detect an immune reaction to *E. canis* in a subject, across a wide variety of genetic variants of this species of *E. canis* bacteria. Methods of using the synthetic peptides provided herein to vaccinate against *E. canis* are also provided.

In some aspects, engineered polypeptides E177 (SEQ ID NO:1) and E208 (SEQ ID NO:7) can display superior properties for diagnosis of *Ehrlichia* as compared to natural *Ehrlichia* polypeptide. For example, as shown in FIG. 1, synthetic polypeptides E177 (SEQ ID NO:1) and E208 (SEQ ID NO:7) can be used to broadly detect exposure to or infection by *E. canis* and *E. chaffeensis* in sera samples taken from dogs that had become sick and were subsequently determined to have been exposed to *Ehrlichia*. Because the dogs had been infected by *E. canis* or *E. chaffeensis* naturally, exposure to a wide variety of *Ehrlichia* variants is included in this data. As shown in FIG. 1, synthetic polypeptides E177 (SEQ ID NO:1) and E208 (SEQ ID NO:7) were more effective than individual immunogenic polypeptide from *Ehrlichia* for detecting infection. E177 demonstrated overall stronger ELISA reactivity with *E. canis* antibodies compared to control peptide #1 (TRP36) in all positive sera (100%) tested. Increased analytical sensitivity of E177 was observed compared control peptide #1 in 22/40 (55%) positive dog sera, which may contribute to improved laboratory and clinical diagnosis, earlier treatment, and improved disease outcome. Background from a pooled negative dog sera (n=10) was subtracted to obtain OD values for positive sera. Cutoff threshold OD>0.01 for positive. E208 displayed higher immunoreactivity than E177 in sera samples from dogs exposed to *Ehrlichia*. E177 and E208 can be utilized together or in combination to obtain superior diagnosis of *Ehrlichia* across a wide variety of *Ehrlichia* variants. As shown in FIGS. 1-3, immunoreactivity of E177 and E208 in some samples (e.g., samples 5, 6, 17, 41) but not in other samples (e.g., 44, 38, 31, 34) demonstrates the ability of the engineered polypeptides to detect coinfections in addition to discriminating between antibodies from distinct *Ehrlichia* spp. Thus, the engineered E177 (SEQ ID NO:1) and E208 (SEQ ID NO:7) polypeptides were observed to display superior immunoreactivity even beyond highly immunogenic polypeptides from naturally occurring *E. chaffeensis* and *E. canis* proteins.

An immunoreactive non-natural polypeptide may comprise any one of SEQ ID NOs:1-7, such as E177 (SEQ ID NO 1) and/or E208 (SEQ ID NO:7). Such polypeptides can be produced by methods including recombinantly, synthetically, or using In Vitro Transcription and Translation (IVTT) methodologies. Any one of SEQ ID NO:1-7 can be included in a non-natural immunoreactive peptide(s), and it is anticipated that these can provide superior diagnostic results for detecting *E. canis* infection. As shown in the below examples, E177 (SEQ ID NO 1) and E208 (SEQ ID NO:7) are non-natural engineered polypeptides that were observed to display a superior ability to diagnose infection by a wide variety of genetic variants of *Ehrlichia*, even compared to highly immunoreactive antigenic regions from naturally occurring protein (highly immunoreactive TRP36 from *E. canis*). Without wishing to be bound by any theory, it is anticipated that SEQ ID NO:6 contained within SEQ ID NO:1 may contribute to the effectiveness of SEQ ID NO:1. E177 (SEQ ID NO 1) and E208 (SEQ ID NO:7) proteins can display improvements even over naturally occurring immunogenic regions of *Ehrlichia* proteins that are highly immunoreactive, as shown in the high stringency testing performed in FIG. 1, and these engineered polypeptides (e.g., SEQ ID NO:1-7, in some preferred embodiments SEQ ID NO:1 and SEQ ID NO:7) can provide advantages for diagnosis of *E. chaffeensis* and *E. canis* in a mammalian subject (e.g., a dog or human).

TABLE 1

| Immunoreactive Peptides |
|---|
| (SEQ ID NO:1; E177)<br>TEDSVSAPATEDSVSAPATEDSVSAPATEDSVSAPATEDSVSAPATEDS<br>VSAPAGGGSYNHNTGLLDLDSDILNMLYSYNHNTGLLDLDSDILNMLYS<br>YNHNTGLLDLDSDILNMLYGGGSKEESTPEVKAEDLQPAVDSKEESTPE<br>VKAEDLQPAVDSKEESTPEVKAEDLQPAVD |
| (SEQ ID NO: 2)<br>SYNHNTGLLDLDSDILNMLYSYNHNTGLLDLDSDILNMLYGGGSKEEST<br>PEVKAEDLQPAVDSKEESTPEVKAEDLQPAVD |
| (SEQ ID NO: 3)<br>SKEESTPEVKAEDLQPAVDSKEESTPEVKAEDLQPAVDGGGSYNHNTGL<br>LDLDSDILNMLYSYNHNTGLLDLDSDILNMLY |
| (SEQ ID NO: 4)<br>TEDSVSAPATEDSVSAPAGGGSYNHNTGLLDLDSDILNMLYSYNHNTGL<br>LDLDSDILNMLY |

TABLE 1-continued

| Immunoreactive Peptides |
|---|
| (SEQ ID NO: 5)<br>SYNHNTGLLDLDSDILNMLYSYNHNTGLLDLDSDILNMLYGGGTEDSVS<br>APATEDSVSAPA |
| (SEQ ID NO: 6)<br>SYNHNTGLLDLDSDILNMLYSYNHNTGLLDLDSDILNMLY |
| (SEQ ID NO:7; E208)<br>SKVEQEETNPEVLIKDLQDVASSKVEQEETNPEVLIKDLQDVASSKVEQ<br>EETNPEVLIKDLQDVASSKVEQEETNPEVLIKDLQDVASGGGDKNKLQD<br>VKDNKPSDVKLPVIKAEDKNKLQDVKDNKPSDVKLPVIKAEDKSKLRDV<br>KDNKPSDVKLPVVKAEDKNKLQDVKDNKPSDVKLPVIKAEDKSKLRDVK<br>DNKPSDVKLPVVKAE |

An aspect of the present disclosure relates to an immunoreactive polypeptide comprising any one of SEQ ID NO:1-7, in some preferred embodiments SEQ ID NO:1 or SEQ ID NO:7, or a polypeptide at least 90% identical (e.g., at least 90, 91, 92, 93, 94, 95, 96, 97, 98, 99%, or 99.5% identical) thereto. In some embodiments, the polypeptide comprises SEQ ID NO2, SEQ ID NO:3, or SEQ ID NO:4. The polypeptide may comprise SEQ ID NO2 and SEQ ID NO:4. In some preferred embodiments, the polypeptide comprises or consists of SEQ ID NO:1 or SEQ ID NO:7. The polypeptide may comprise SEQ ID NO: 6. The polypeptide may comprise SEQ ID NO:7. In some preferred embodiments, the polypeptide is less than 500, less than 450, less than 400, less than 350, less than 300, or less than 250 amino acids in length. The polypeptide may be comprised in a pharmaceutical preparation. The pharmaceutical preparation may be formulated for parenteral, intravenous, subcutaneous, intranasal, sublingual, or intradermal administration. In some embodiments, the polypeptide is attached to a solid support or comprised in a diagnostic kit. The solid support may be glass or plastic. The solid support may be comprised in a lateral flow assay, or microfluidic device. In some embodiments, the solid support is a microarray or a protein chip. The polypeptide may be covalently bound to an epitope tag (e.g., ALFA-tag, V5-tag, Myc-tag, HA-tag, Spot-tag, T7-tag or NE-tag) or a fluorescent label (e.g., a green fluorescent protein (GFP), red fluorescent protein (RFP), Halo, SNAP, or CLIP).

Another aspect of the present disclosure relates to a pharmaceutical preparation comprising a polypeptide described above or herein and a pharmaceutically acceptable excipient.

The pharmaceutical preparation may be formulated for parenteral, intravenous, subcutaneous, intranasal, sublingual, or intradermal administration. The pharmaceutically acceptable excipient may comprise an adjuvant. The adjuvant may be an emulsion or liposomes, or wherein the adjuvant comprises a lipid. The emulsion may be an oil-in-water (O/W) emulsion or a water-in-oil (W/O) emulsion. In some embodiments, the adjuvant comprises a triterpenoid, a sterol, an immunomodulator, a polymer, and/or an immunostimulatory oligonucleotide. The polymer may be diethylaminoethyl (DEAE)-dextran, polyethelyne glycol, or polyacrylic acid. In some embodiments, the immunostimulatory oligonucleotide is a CpG containing ODN. In some embodiments, the adjuvant comprises a saponin, a sterol, a quaternary ammonium compound, a polymer, and an ORN/ODN. In some embodiments, the saponin is Quil A or a purified faction thereof, the sterol is cholesterol, the quaternary ammonium compound is dimethyl dioctadecyl ammonium bromide (DDA), the polymer is polyacrylic acid, and the ORN/ODN is a CpG. In some embodiments, the saponin is present in an amount of about 1 μg to about 5,000 μg per dose, the sterol is present in an amount of about 1 μg to about 5,000 μg per dose, the quaternary ammonium compound is present in an amount of about 1 μg to about 5,000 μg per dose, and the polymer is present in an amount of about 0.0001% v/v to about 75% v/v. The adjuvant may further comprise a glycolipid (e.g., N-(2-deoxy-2-L-leucylamino-β-D-glucopyranosyl)-N-octadecyldodecanamide acetate). In some embodiments, the adjuvant comprises a triterpenoid saponin, a sterol, a quaternary ammonium compound, and a polyacrylic acid polymer. In some embodiments, the saponin is Quil A or a purified fraction thereof, the sterol is cholesterol, and the quaternary ammonium compound is dimethyl dioctadecyl ammonium bromide (DDA). In some embodiments, the saponin is present in an amount of about 1 mg to about 5,000 mg per dose, the sterol is present in an amount of about 1 mg to about 5,000 mg per dose, the quaternary ammonium compound is present in an amount of about 1 mg to about 5,000 mg per dose, and the polyacrylic acid polymer is present in an amount of about 0.0001% v/v to about 75% v/v. The adjuvant may comprise or be MF59, AS01, AS02, AS03, AS04, Virosomes, CAF01, CAF04, CAF05, an acrylic polymer/DDA emulsion, a CpG/DEAE emulsion, a saponin/cholesterol/DDA adjuvant, or a polyacrylic acid polymer emulsion. The composition may further comprises an *Ehrlichia* bacterin (e.g., a heat-inactivated *E. canis*, a chemically-inactivated *E. canis*, a heat-inactivated *E. chaffeensis*, or a chemically-inactivated *E. chaffeensis*).

Yet another aspect of the present disclosure relates to a nucleic acid encoding a polypeptide described above or herein. The nucleic acid may be a DNA segment or an RNA. The RNA may comprise one or more chemical modification. In some embodiments, the nucleic acid is comprised in an expression vector. For example, in some embodiments, the nucleic acid is an RNA that can be included in an RNA vaccine to generate an immune response against an *Ehrlichia* organism in a mammalian subject such as a dog or human.

Another aspect of the present disclosure relates to a host cell comprising the nucleic acid described above or herein. In some embodiments, the cell expresses the nucleic acid.

Yet another aspect of the present invention relates to a method of detecting antibodies that specifically bind an *Ehrlichia* organism in a test sample, comprising: (a) contacting an isolated polypeptide described above or herein to the test sample; (b) detecting the peptide-antibody complexes; wherein the detection of the peptide-antibody complexes is an indication that antibodies specific for an *Ehrlichia* organism are present in the test sample. In some embodiments, the absence of the peptide-antibody complexes is an indication that antibodies specific an *Ehrlichia* organism are not present in the test sample. The *Ehrlichia* organism may be an *Ehrlichia chaffeensis* organism or an *Ehrlichia canis* organism. The step of detecting may comprise performing an enzyme-linked immunoassay, a radioimmunoassay, an immunoprecipitation, a fluorescence immunoassay, a chemiluminescent assay, an immunoblot assay, a lateral flow assay, a flow cytometry assay, a multiplex immunoassay, a mass spectrometry assay, or a particulate-based assay. The step of detecting may comprise a lateral flow assay or an enzyme-linked immunoassay. In some preferred embodiments, the enzyme-linked immunoassay is an ELISA. The step of detecting may be performed on a protein microarray or a protein chip. The test sample may be biological sample such as a blood, serum, or plasma sample. The test sample may be a biological sample obtained from a dog or a human.

Another aspect of the present disclosure relates to a method of identifying an *Ehrlichia* infection in a mammalian subject comprising: (a) contacting a biological sample from the subject with an isolated polypeptide described above or herein (e.g., comprising any one of SEQ ID NOs:1-7, in some preferred embodiments SEQ ID NO:1 or SEQ ID NO:7) under conditions that allow peptide-antibody complexes to form; and (b) detecting the peptide-antibody complexes; wherein the detection of the peptide-antibody complexes is an indication that the subject has an *Ehrlichia* infection. The step of detecting may comprise performing an enzyme-linked immunoassay, a radioimmunoassay, an immunoprecipitation, a fluorescence immunoassay, a chemiluminescent assay, an immunoblot assay, a lateral flow assay, a flow cytometry assay, a multiplex immunoassay, a dipstick test, or a particulate-based assay. The subject may be preferably a human or a dog.

Yet another aspect of the present disclosure relates to a kit comprising: (a) the isolated polypeptide described above or herein (e.g., comprising any one of SEQ ID NOs:1-7, such as SEQ ID NO:1 or SEQ ID NO:7), (b) an anti-dog or anti-human secondary antibody linked to a reporter molecule; and, (c) an appropriate reagent for detection of the reporter molecule. The peptide may be immobilized on a membrane, on a microtiter plate, on a protein microarray, or on a protein chip. The reporter molecule may be selected from the group consisting of luciferase, horseradish peroxidase, a luminous nanoparticle, P-galactosidase, and a fluorescent label. The luminous nanoparticle may be a strontium aluminate nanoparticle. The kit may further comprise a dilution buffer for dog or human serum. The kit may comprise an immunoassay, such as a lateral flow immunoassay, or a lateral flow immunochromatographic assay. The kit may comprise an enzyme-linked immunosorbent assay (ELISA).

Another aspect of the present disclosure relates to a method of inducing an immune response in a mammalian subject comprising administering to the subject an effective amount of a pharmaceutical preparation comprising a polypeptide described above or herein (e.g., comprising any one of SEQ ID NOs:1-7, in some preferred embodiments SEQ ID NO:1 or SEQ ID NO:7), or a pharmaceutical composition described above or herein. The subject may be a human or a dog. The pharmaceutical preparation may be administered subcutaneously, intramuscularly, nasally, via inhalation or aerosol delivery, or intradermally.

Yet another aspect of the present disclosure relates to a method of treating an *Ehrlichia chaffeensis* or *Ehrlichia canis* infection in a subject comprising: (a) contacting a biological sample from the subject with an isolated polypeptide described above or herein (e.g., comprising any one of SEQ ID NOs:1-7, in some preferred embodiments SEQ ID NO:1 or SEQ ID NO:7) under conditions that allow peptide-antibody complexes to form; (b) detecting the peptide-antibody complexes; wherein the detection of the peptide-antibody complexes is an indication that the subject has an *Ehrlichia chaffeensis* or *Ehrlichia canis* infection; and (c) administering a therapeutic compound to treat *Ehrlichia* infection in the subject. The step of detecting may comprise performing an enzyme-linked immunoassay, a radioimmunoassay, an immunoprecipitation, a fluorescence immunoassay, a chemiluminescent assay, an immunoblot assay, a lateral flow assay, a flow cytometry assay, a multiplex immunoassay, a dipstick test, or a particulate-based assay.

The subject may be a dog or a human. The therapeutic compound may be an antibiotic (e.g., doxycycline).

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the inherent variation in the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

I. Engineered Immunoreactive Polypeptides

Figure 1:
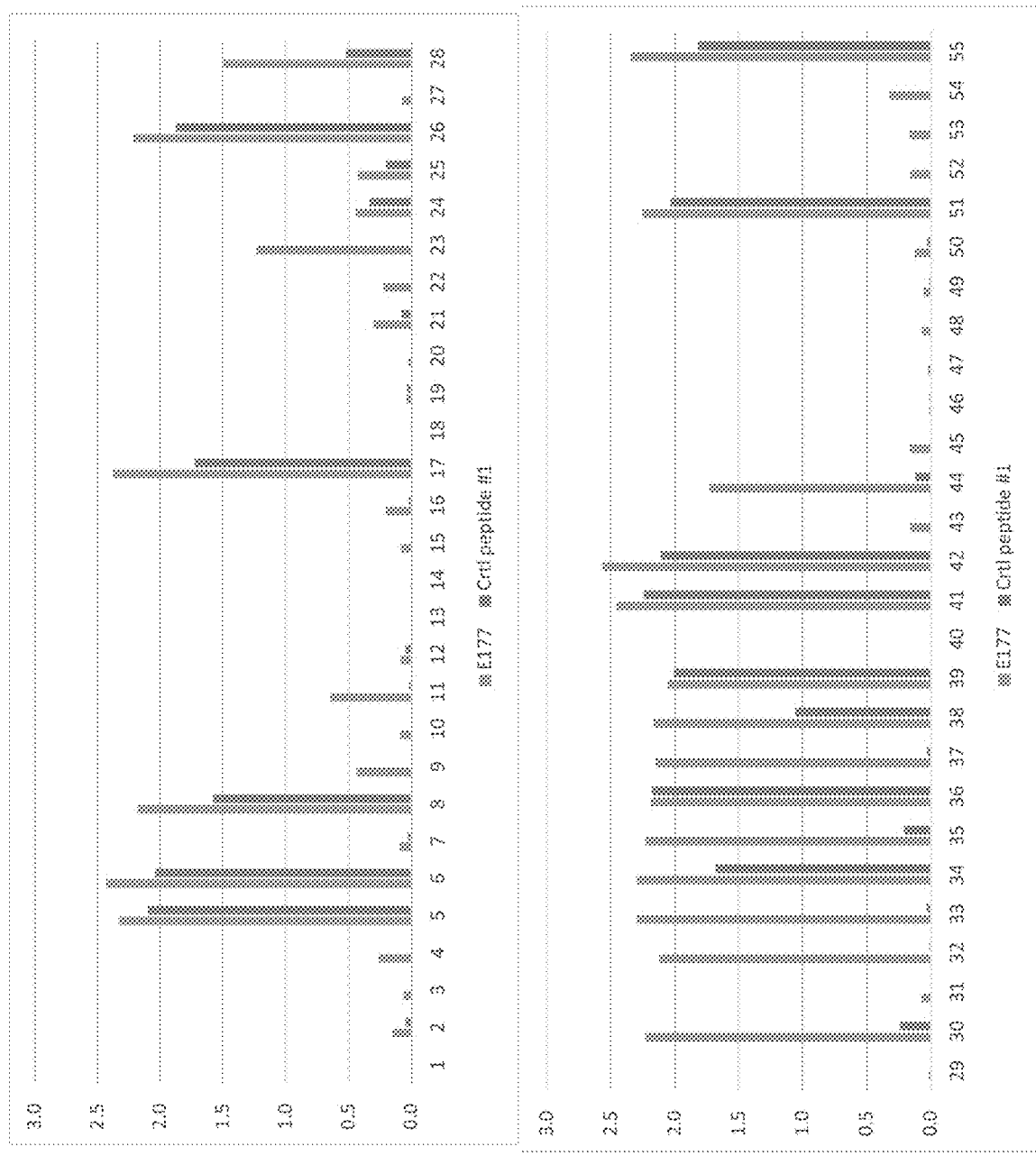
FIG. 1: Detection of *Ehrlichia* immunoreactivity in sera obtained from dogs by ELISA. Each number at the X-axis indicates a different subject. Serum samples from each dog were tested against the different antigens for immunoreactivity. Results using the E177 (SEQ ID NO:1) or a highly immunoreactive control peptide ("Crtl peptide #1"; SEQ ID NO:8) are shown.
Figure 2:
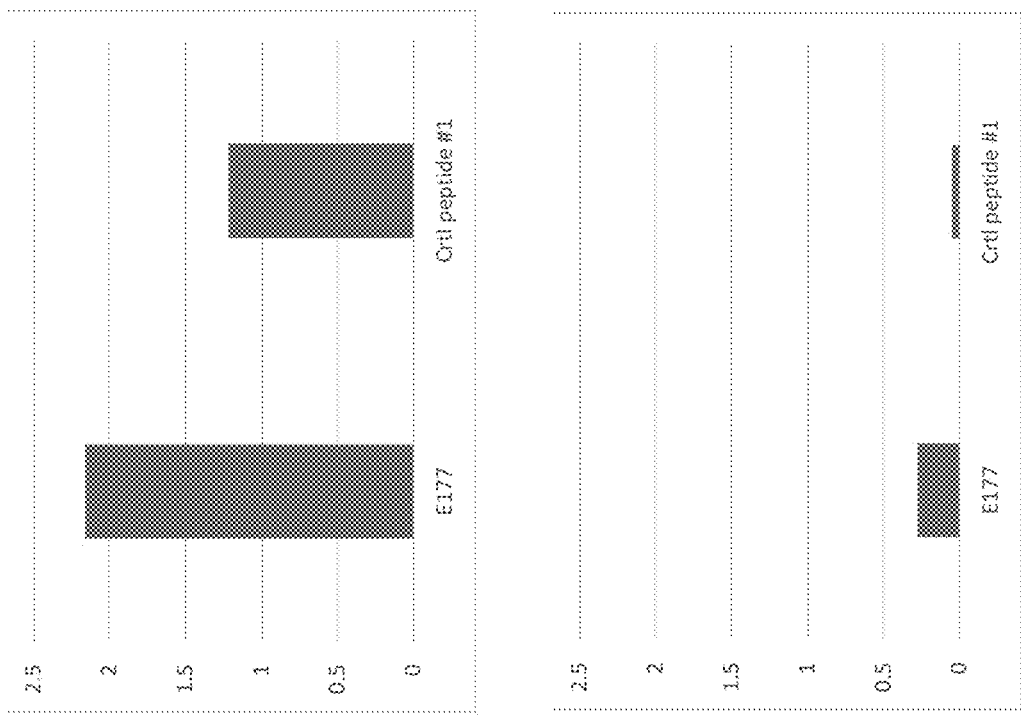
FIG. 2: Results from highly immunoreactive and low immunoreactivity samples are shown. The data from FIG. 1 was classified into highly immunoreactive (top) and low immunoreactivity (bottom) groups. In both groups, the engineered E177 (SEQ ID NO:1) sample displayed increased immunoreactivity as compared to the highly immunoreactive control peptide ("Crtl peptide #1"; SEQ ID NO:8).
Figure 3:
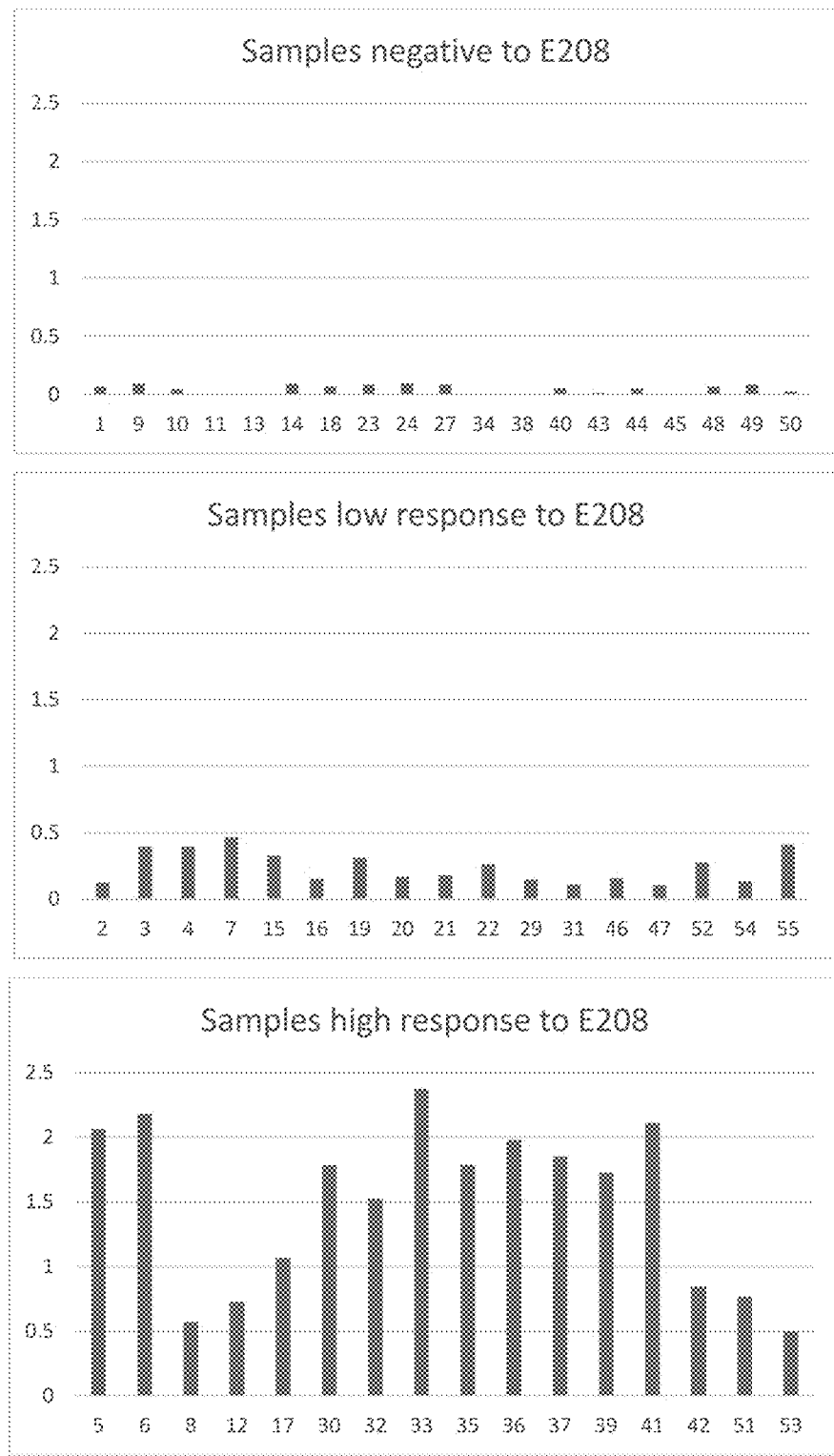
FIG. 3: Immunoreactivity to engineered polypeptide E208 (SEQ ID NO:8). Detection of *Ehrlichia* immunoreactivity in sera obtained from dogs by ELISA. Each number at the X-axis indicates a different subject. Serum samples from each dog were tested against the different antigens for immunoreactivity. Results using the E208 polypeptide are shown.

Immunoreactive polypeptides comprising any one of SEQ ID NOs:1-7, in some preferred embodiments E177 (SEQ ID NO: 1) and/or E208 (SEQ ID NO:7) are provided herein and can be used, e.g., in a diagnostic assay to test for ehrlichiosis or in a vaccine composition to induce an immune response against an *Ehrlichia* spp. organism. In some aspects, nucleic acids encoding the polypeptides are provided. For example, an RNA encoding the immunoreactive polypeptide (e.g., a nucleic acid encoding a polypeptide comprising any one of SEQ ID NOs:1-7, in some preferred embodiments SEQ ID NO:1 or SEQ ID NO:7) can be administered to a mammalian subject to temporarily cause expression of the immunoreactive polypeptide, in order to induce an immune reaction against an *Ehrlichia* spp. organism. The RNA may comprise one or more chemical modifications to increase half-life or resist degradation in the body. The immunoreactive polypeptide can be included in an assay (e.g., an immunoassay, ELISA, enzyme immunoassay (EIAs), etc.) or on a protein array to test a biological sample (e.g., a sera sample) from a mammalian subject (e.g., a dog or a human) for infection by an *Ehrlichia* spp. organism.

In some embodiments, an immunoreactive polypeptide comprising any one of SEQ ID NOs:1-7, in some preferred embodiments E177 (SEQ ID NO 1) and/or E208 (SEQ ID NO:7), may be immobilized onto a surface of a support or a solid substrate; for example, the immunoreactive polypeptide may be immobilized directly or indirectly by coupling, cross-linking, adsorption, encapsulation, or by any appropriate method known in the art. By way of non-limiting example, binding of an immunoreactive polypeptide disclosed herein by adsorption to a well in a microtiter plate or to a membrane may be achieved by contacting the peptide, in a suitable buffer, with the well surface for a suitable amount of time. The contact time can vary with temperature, but is typically between about 1 hour and 1 day when using an amount of peptide ranging from about 50 ng to about 1 mg, and preferably about 250-700 ng or about 450-550 ng.

In some embodiments, an immunoreactive polypeptide disclosed herein is covalently attached to a support substrate by first reacting the support with a reagent that will chemically react with both the support and a functional group (i.e., crosslink), such as a hydroxyl or amino group, on the peptide. For example, an immunoreactive polypeptide may be crosslinked to a surface through an amine or carboxylic group on either end of the peptide, and a peptide may be crosslinked through a group on each end of the polypeptide (i.e., head-to-tail crosslinked). Such peptomers (i.e., head-to-tail crosslinked or otherwise immobilized peptides) may be used with both diagnostic and therapeutic methods of the present disclosure.

In some embodiments, an isolated polypeptide comprising any one of SEQ ID NOs:1-7, in some preferred embodiments E177 (SEQ ID NO 1) and/or E208 (SEQ ID NO:7) is immobilized on a surface of a support substrate. Numerous support substrates for peptide immobilization are known in the art which may be employed with an immunoreactive polypeptide disclosed herein, formed from materials such as, for example, latex, polystyrene, nylon, nitrocellulose, cellulose, silica, agarose, inorganic polymers, lipids, proteins, sugars, or magnetic resin. A person of ordinary skill in the art may select the support substrate that is appropriate for a given application. In particular embodiments, a support substrate may be a reaction chamber, a microplate well, a membrane, a filter, a paper, an emulsion, a bead, a microbead, a microsphere, a nanocrystal, a nanosphere, a dipstick, a card, a glass slide, a microslide, a lateral flow apparatus, a microchip, a comb, a silica particle, a magnetic particle, a nanoparticle, or a self-assembling monolayer.

II. Detectably-Labeled Immunoreactive Polypeptides

An immunoreactive polypeptide comprising any one of SEQ ID NOs:1-7, in some preferred embodiments E177 (SEQ ID NO 1) and/or E208 (SEQ ID NO:7), may be conjugated to or attached to a detectable label such as, for example, a radioactive isotope, a non-radioactive isotope, a particulate label, a fluorescent label, a chemiluminescent label, a paramagnetic label, an enzyme label or a colorimetric label. The detectably-labelled polypeptide may be used, e.g., in diagnostic or prophylactic methods and compositions. In certain embodiments, the polypeptide portion of the detectably labeled immunoreactive polypeptide may be immobilized on a surface of a support substrate. In other embodiments, the detectable label may be used to immobilize the detectably labeled immunoreactive peptide to the surface of a support substrate.

As used herein, "detectable label" is a compound and/or element that can be detected due to its specific functional properties, and/or chemical characteristics, the use of which allows the peptide to which it is attached be detected, and/or further quantified if desired.

In some embodiments, the probe is a photoluminescent probe, such as a fluorophore or a nanoparticle, such as for example a strontium aluminate nanoparticle (e.g., see Paterson et al., 2014). Exemplary labels include, but are not limited to, a particulate label such as colloidal gold, a radioactive isotope such as astatine$^{211}$, $^{14}$carbon, $^{51}$chromium, $^{36}$chlorine, $^{57}$cobalt, $^{58}$cobalt, copper$^{67}$, 152$^{Eu}$, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium-99, technetium-99m or yttrium$^{90}$, a colorimetric label such as dinitrobenzene, dansyl chloride, dabsyl chloride, any of the azo, cyanin or triazine dyes, or chromophores disclosed in U.S. Pat. Nos. 5,470,932, 5,543,504, or 6,372,445, all of which are incorporated herein by reference; a paramagnetic label such as chromium (II), manganese (II), iron (11), iron (ID), cobalt (ID), nickel (I), copper (1D, neodymium (1), samarium (I), ytterbium (II), gadolinium (IID), vanadium (11), terbium (III), dysprosium (I), holmium (I) or erbium (IID, a fluorescent label such as Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, or Lucifer Yellow, an enzyme label such as urease, luciferase, alkaline phosphatase, (horseradish) hydrogen peroxidase, or glucose oxidase, or a chemiluminescent label such as luminol, phthalazinedione, and others disclosed in any of U.S. Pat. Nos. 4,373,932, 4,220,450, 5,470,723, and U.S. Patent Application 2007/0264664 now U.S. Pat. No. 7,732,153, all of which are incorporated herein by reference.

III. Methods of Producing an Immunoreactive Polypeptide

An immunoreactive polypeptide comprising any one of SEQ ID NOs:1-7, in some preferred embodiments E177 (SEQ ID NO 1) and/or E208 (SEQ ID NO:7), may be produced using in vitro transcription and translation (IVTT) methods, may be recombinantly produced using a variety of cell types (e.g., bacterial cells, mammalian cells, E. coli, yeast, and insect cells, etc.), or in some instances may be synthesized (e.g., using solid-phase synthesis). In some embodiments, IVTT and synthetic methods can provide certain advantages over recombinant approaches, since the resulting polypeptides can produced highly pure forms without contaminating bacterial or other proteins that might result in false positive reactions when utilizing recombinant proteins. Thus, IVTT and synthetic methods have an advantage of lacking many of the costly and laborious purification procedures often associated with recombinant methodologies. In some embodiments, the polypeptide is covalently bound to or directly synthesized on a protein microarray (e.g., comprising a glass solid surface) or a protein chip.

A variety of IVTT approaches are known in the art and may be used in various embodiments. IVTT generally involves cell-free methods for production or synthesis of a protein from DNA. The cell-free system for protein production may use, e.g., E. coli extract, protozoan extracts, yeast extracts, human cell extract, wheat germ extract, mammalian extracts, extracts from cultured human cell lines, rabbit reticulocyte lysate, insect cell extract, or reconstituted and purified E. coli components. A variety of kits are commercially available including, e.g., RTS (FivePrime, San Francisco, CA), Expressway™ (Life Technologies); S30 T7 high yield (Promega), One-step human IVT (Thermo Scientific), WEPRO® (CellFree Sciences), TNT® coupled (Promega), RTS CECF (5 PRIME), TNT® Coupled (Promega), Retic lysate IVT™ (Life Technologies); TNT® T7 (Promega), EasyXpress Insect kit (Qiagen/RiN A), PURExpress® (New England Biolabs), and PURESYSTEM® (BioComber). Such methods can be used to incorporate unnatural amino acids into proteins, if desired. Cell-free expression systems that may be used in various embodiments are also described, e.g., in Zemella et al., 2015.

An isolated immunoreactive protein as disclosed herein may be produced in some embodiments using an appropriate method known in the organic chemistry arts. For example, peptides may be produced using one of the established solid-phase peptide synthesis techniques that are well known in the art. In some embodiments, peptides may be synthesized using equipment for automated peptide synthesis that is widely available from commercial suppliers such as Perkin Elmer (Foster City, CA), or the peptide may be chemically synthesized using solution-phase techniques such as those described in Carpino et al., 2003 or U.S. Patent Application 2009/0005535 now U.S. Pat. No. 8,013,117. In some embodiments, the peptides or shorter proteins may be synthesized, e.g., using solid-phase peptide synthesis (SPPS), t-Boc solid-phase peptide synthesis, or Fmoc solid-phase peptide synthesis.

In some embodiments, an immunoreactive protein as described herein can be recombinantly prepared from a nucleic acid encoding the peptide. Such a nucleic acid may be operably linked to an expression vector. By way of nonlimiting example, an immunoreactive protein may be expressed from a vector and isolated from the growth media of a host cell comprising the vector. In some embodiments, the immunoreactive protein may be produced in a cell-free system from a nucleic acid encoding the peptide.

An immobilized immunoreactive protein as disclosed herein may be conjugated, crosslinked, or adsorbed, either directly or indirectly onto a surface of a support substrate. In some embodiments, an immobilized immunoreactive protein or peptide may be synthesized onto a support substrate.

It is anticipated that virtually any method of protein or peptide immobilization known in the art which would not impact the structure or function of the disclosed peptides may be used to immobilize an immunoreactive protein or peptide as disclosed herein. For example, peptide immobilization may be accomplished using a crosslinking or conjugation agent such as methyl-p-hydroxybenzimidate, N-succinimidyl-3-(4-hydroxyphenyl)propionate, using sulfosuccinimidyl 4-(N-maleimidomethyl)cyclohexane-1-carboxylate (sSMCC), N-[maleimidocaproyloxy]sulfosuccinimide ester (sEMCS), N-maleimidobenzoyl-N-hydroxysuccinimide ester (MBS), glutaraldehyde, 1-ethyl-3-(3-dimethylaminopropyl) carbodiimide (EDCI), Bis-diazobenzidine (BDB), or N-acetyl homocysteine thiolactone (NAHT), and others disclosed in any of U.S. Pat. Nos. 5,853,744, 5,891,506, 6,210,708, 6,617,142, 6,875,750, 6,951,765, 7,163,677, and 7,282,194, each incorporated herein by reference. Immunoreactive proteins may be conjugated directly or indirectly to any of the commercially available support substrates having a surface coating comprising crosslinkers, coupling agents, thiol or hydroxyl derivatizing agents, carboxyl- or amine-reactive groups such as of maleic anhydride (e.g., Pierce Immunotechnology Catalog and Handbook, at A12-A13, 1991).

In some embodiments, a protein of the invention may also be immobilized using metal chelate complexation, employing, for example, an organic chelating agent such a diethylenetriaminepentaacetic acid anhydride (DTPA); EDTA; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Proteins and peptides can also be immobilized by coupling to other peptides or to condensation groups immobilized on a surface or present in an immobilization buffer such as glutaraldehyde or periodate. Conjugates with fluorescence markers may also be prepared in the presence of such agents or by reaction with an isothiocyanate. A peptide may be attached to a surface by conjugation, crosslinking or binding to an affinity binding agent such as biotin, streptavidin, a polysaccharide such as an alginate, a lectin, and the like.

In general, regardless of the method of preparation or immobilization status, the immunoreactive proteins disclosed herein are preferably prepared in a substantially pure form.

Preferably, the immunoreactive proteins are at least about 80% pure, more preferably at least about 90% pure and most preferably at least about 99% pure.

IV. Biological Functional Equivalents

Biological functional equivalents of any one of SEQ ID NOs:1-7, E177 (SEQ ID NO 1) and/or E208 (SEQ ID NO:7), are also provided herein. For example it is anticipated that a polypeptide having at least 85%, 90, 91, 92, 93, 94, 95, 96, 97, 98, 99, or 99.5 percent sequence identity to any one of SEQ ID NOs:1-7, E177 (SEQ ID NO 1) and/or E208 (SEQ ID NO:7), may bind an *E chaffeensis* or *E. canis* specific antibody and can be used in an immunological assay to detect exposure to *E. chaffeensis* or *E. canis*. The any one of SEQ ID NOs:1-7, E177 (SEQ ID NO 1) and/or E208 (SEQ ID NO:7), or a polypeptide having at least 85%, 90, 91, 92, 93, 94, 95, 96, 97, 98, 99, or 99.5 percent sequence identity thereto can be included in a variety of in vitro assay such as, for example, an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (FA), nephelometry, flow cytometry assay, chemiluminescence assay, lateral flow immunoassay, u-capture assay, mass spectrometry assay, particle-based assay, inhibition assay and/or an avidity assay.

An immunoreactive polypeptide of the present disclosure such as SEQ ID NOs:1-7, E177 (SEQ ID NO 1) and/or E208 (SEQ ID NO:7), may be modified to contain amino acid substitutions, insertions and/or deletions that do not alter their respective interactions with anti-*Ehrlichia* antibody binding regions. Such a biologically functional equivalent of an immunoreactive polypeptide derived from an *Ehrlichia* protein could be a molecule having like or otherwise desirable characteristics, i.e., binding of *Ehrlichia* specific antibodies. As a nonlimiting example, certain amino acids may be substituted for other amino acids in an immunoreactive polypeptide disclosed herein without appreciable loss of interactive capacity, as demonstrated by detectably unchanged antibody binding. It is thus contemplated that an immunoreactive polypeptide disclosed herein (or a nucleic acid encoding such a polypeptide) which is modified in sequence and/or structure, but which is unchanged in biological utility or activity, remains within the scope of the present disclosure. The immunoreactive polypeptide may have, e.g., at least 90%, 95%, 97%, 99%, or 99.5% sequence identity with any one of SEQ ID NOs:1-7, E177 (SEQ ID NO 1) and/or E208 (SEQ ID NO:7), and in some embodiments the immunoreactive protein may have 1, 2, 3, 4, 5, or more amino acid substitutions, insertions and/or deletions as compared with any one of SEQ ID NOs:1-7, E177 (SEQ ID NO 1) and/or E208 (SEQ ID NO:7). In some embodiments, the mutation is a conservative substitution.

It is also well understood by the skilled artisan that, inherent in the definition of a biologically functional equivalent peptide, is the concept that there is a limit to the number of changes that may be made within a defined portion of the molecule while still maintaining an acceptable level of equivalent biological activity. Biologically functional equivalent polypeptides are thus defined herein as those peptides in which certain, not most or all, of the amino acids may be substituted. Of course, a plurality of distinct peptides with different substitutions may easily be made and used in accordance with the invention.

The skilled artisan is also aware that where certain residues are shown to be particularly important to the biological or structural properties of a peptide, e.g., residues in specific epitopes, such residues may not generally be exchanged. It is anticipated that a mutation in an immunoreactive peptide or polypeptide disclosed herein could result in a loss of species-specificity and in turn, reduce the utility of the resulting peptide for use in methods for generating an anti-*Ehrlichia* immune response. Thus, polypeptides which are antigenic (i.e., bind anti-*Ehrlichia* antibodies specifically) and comprise conservative amino acid substitutions are understood to be included in aspects of the present disclosure. Conservative substitutions are least likely to drastically alter the activity of a protein. A "conservative amino acid substitution" refers to replacement of amino acid with a chemically similar amino acid, i.e., replacing nonpolar amino acids with other nonpolar amino acids; substitution of polar amino acids with other polar amino acids, acidic residues with other acidic amino acids, etc.

Amino acid substitutions, such as those which might be employed in modifying an immunoreactive polypeptide disclosed herein are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

The invention also contemplates isoforms of SEQ ID NOs:1-7, E177 (SEQ ID NO 1) and/or E208 (SEQ ID NO:7). An isoform contains the same number and kinds of amino acids as an immunoreactive polypeptide as disclosed herein, but the isoform has a different molecular structure. The isoforms contemplated by the present disclosure are those having the same properties as a peptide of the invention as described herein.

Nonstandard amino acids may be incorporated into proteins by chemical modification of existing amino acids or by de novo synthesis of a polypeptide disclosed herein. A nonstandard amino acid refers to an amino acid that differs in chemical structure from the twenty standard amino acids encoded by the genetic code, and a variety of nonstandard amino acids are well known in the art.

In select embodiments, the present disclosure contemplates a chemical derivative of an immunoreactive polypeptide disclosed herein. "Chemical derivative" refers to a peptide having one or more residues chemically derivatized by reaction of a functional side group and retaining biological activity and utility. Such derivatized polypeptides include, for example, those in which free amino groups have been derivatized to form specific salts or derivatized by alkylation and/or acylation, p-toluene sulfonyl groups, carbobenzoxy groups, t-butylocycarbonyl groups, chloroacetyl groups, formyl or acetyl groups among others. Free carboxyl groups may be derivatized to form organic or inorganic salts, methyl and ethyl esters or other types of esters or hydrazides and preferably amides (primary or secondary). Chemical derivatives may include polypeptides that comprise one or more naturally occurring amino acids derivatives of the twenty standard amino acids. For example, 4-hydroxyproline may be substituted for serine; and ornithine may be substituted for lysine.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The amino acids described herein are preferred to be in the "L" isomeric form. However, residues in the "D" isomeric form can be substituted for any L-amino acid residue, if the desired functional properties set forth herein are retained by the protein. In keeping with standard protein nomenclature, abbreviations for amino acid residues are known in the art.

In addition to the biological functional equivalents discussed above, it is contemplated that structurally similar compounds may be formulated to mimic the key portions of an immunoreactive peptide disclosed herein. Such compounds, which may be termed peptidomimetics, may be used in the same manner as immunoreactive peptides disclosed herein and, hence, also are functional equivalents. Methods for generating specific structures are disclosed, e.g., in Mizuno et al., 2017, as well as in U.S. Pat. Nos. 5,446,128; 5,710,245; 5,840,833; 5,859,184; 5,440,013; 5,618,914; and 5,670,155.

V. Diagnostic Methods

Ehrlichiosis in humans generally refers to infections caused by obligate intracellular bacteria in the family Anaplasmataceae, chiefly in the genera *Ehrlichia* and *Anaplasma*. The majority of cases of human ehrlichiosis (HE) are caused by 3 distinct species: *Ehrlichia chaffeensis*, chief among them (Dumler et al., 2007). *Ehrlichia* infections in animals are also referred to as ehrlichiosis, along with a variety of diseases caused by a diverse group of pathogens from genera *Ehrlichia, Anaplasma, Neorickettsia*, and *Cowdria* (Dumler et al., 2007). *Ehrlichia* infections are sustained mostly in monocytes or granulocytes, and studies have demonstrated that antibodies play an essential role in the immune response to *Ehrlichia* infection (Feng and Walker, 2004; Winslow et al., 2003; Winslow et al., 2000; Yager et al., 2005).

Accordingly, select embodiments of the present disclosure provide methods of detecting antibodies that specifically bind an *Ehrlichia* organism in a sample. Such a method may involve contacting an isolated immunoreactive polypeptide comprising any one of SEQ ID NOs:1-7, E177 (SEQ ID NO 1) and/or E208 (SEQ ID NO:7), with the test sample, under conditions that allow peptide-antibody complexes to form and detecting the peptide-antibody complexes. In these embodiments, the detection of the peptide-antibody complexes is an indication that antibodies specific for an *Ehrlichia* organism are present in the test sample, and the absence of the peptide-antibody complexes is an indication that antibodies specific an *Ehrlichia* organism are not present in the test sample.

A polypeptide comprising any one of SEQ ID NOs:1-7, E177 (SEQ ID NO 1) and/or E208 (SEQ ID NO:7), can be used in an immunoassay or diagnostic test to detect exposure to or antibodies against *E. chaffeensis* and/or *E. canis*. The detection of antibodies and/or antigens may be achieved by immunoassays, including any immunoassay known in the art including, but not limited to, radioimmunoassay, enzyme-linked immunosorbent assay (ELISA) (e.g., a sandwich ELISA, or a competitive ELISA), precipitin reaction, agglutination assay, fluorescent immunoassay, and chemiluminescence-based immunoassay. In some embodiments, the polypeptide-antibody complex may be assessed by a sandwich or competitive assay format, optionally with a binder or antibody. In some embodiments, the binder or antibody may be attached to a surface and functions as a capture antibody. In some embodiments, the capture binder or antibody may be attached to the surface directly or indirectly. In some embodiments, the binder or antibody may be attached to the surface via a biotin-avidin (or streptavidin) linking pair. In some embodiments, at least one of the binders or antibodies may be labeled. In some embodiments, the polypeptide-antibody complex may be assessed by a format selected from the group consisting of an enzyme-linked immunosorbent assay (ELISA), Western blotting, immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, plasmon resonance assay, chemiluminescence assay, lateral flow immunoassay, u-capture assay, inhibition assay and avidity assay. In some embodiments, the polypeptide-antibody complex may be assessed in a homogeneous or a heterogeneous assay format. The polypeptide may also be used in an immunoblot assay, a lateral flow assay (e.g., using an ELISA type detection method), a mass spectrometry assay, latex agglutination, an indirect hemagglutination assay (IHA), complement fixation, an inhibition assay, an avidity assay, a dipstick test, a flow cytometry assay, or a particular-based assay.

In some embodiments, multiple reagents for detecting infectious organisms may be included in the same assay, such as parallel immunoassay. A parallel immunoassay may include at least 2, 3, 4, 5, 10, 100, 1000 or more reagents, such as antibodies or antigenic polypeptides, in the same assay system.

Numerous technological platforms for performing parallel immunoassays are known. Generally, such methods involve a logical or physical array of either the subject samples, or the protein markers, or both. Common array formats include both liquid and solid phase arrays. For example, assays employing liquid phase arrays, e.g., for hybridization of nucleic acids, binding of antibodies or other receptors to ligand, etc., can be performed in multiwell or microtiter plates. Microtiter plates with 96, 384 or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis. Exemplary systems include, e.g., the ORCA™ system from Beckman-Coulter, Inc. (Fullerton, Calif.) and the Zymate systems from Zymark Corporation (Hopkinton, Mass.).

Alternatively, a variety of solid phase arrays can favorably be employed for parallel immunoassays in the context of the invention. Exemplary formats include membrane or filter arrays (e.g., nitrocellulose, nylon), pin arrays, and bead arrays (e.g., in a liquid "slurry"). Typically, probes corresponding to nucleic acid or protein reagents that specifically interact with (e.g., hybridize to or bind to) an expression product corresponding to a member of the candidate library, are immobilized, for example by direct or indirect cross-linking to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

The polypeptides/antibodies may be immobilized to a solid phase support for the detection of antibody binding. As used herein, "solid phase support" is not limited to a specific type of support. Rather a large number of supports are available and are known to one of ordinary skill in the art. Solid phase supports include silica gels, resins, derivatized plastic films, glass beads, cotton, plastic beads and alumina gels. A suitable solid phase support may be selected on the basis of desired end use and suitability for various synthetic protocols. For example, for peptide synthesis, solid phase support may refer to resins such as polystyrene (e.g., PAM-resin obtained from Bachem Inc., Peninsula Laboratories, etc.), POLYHIPE resin (obtained from Aminotech, Canada), polyamide resin (obtained from Peninsula Laboratories), polystyrene resin grafted with polyethylene glycol (Tenta-Gel, Rapp Polymere, Tubingen, Germany) or polydimethylacrylamide resin (obtained from Milligen/Biosearch, California). In some preferred embodiments, the solid phase support is polydimethylacrylamide resin which may, e.g., be used for peptide synthesis to synthesize or attach one or more of the polypeptides provided herein directly to the solid support.

In one embodiment, the array may be a "chip" composed, e.g., of one of the above-specified materials. Polynucleotide probes, e.g., RNA or DNA, such as cDNA, synthetic oligonucleotides, and the like, or binding proteins such as antibodies or antigen-binding fragments or derivatives thereof may be affixed to the chip in a logically ordered manner, i.e., in an array. Detailed discussions of methods for linking nucleic acids and proteins to a chip substrate, are found in, e.g., U.S. Pat. Nos. 5,143,854, 5,837,832, 6,087,112, 5,215,882, 5,707,807, 5,807,522, 5,958,342, 5,994,076, 6,004,755, 6,048,695, 6,060,240, 6,090,556, and 6,040,138, each of which is hereby incorporated in its entirety.

In some embodiments, an engineered immunoreactive polypeptide provided herein (e.g., a polypeptide comprising any one of SEQ ID NOs:1-7, E177 (SEQ ID NO 1) and/or E208 (SEQ ID NO:7)) is attached to a solid support on a protein microarray. Protein microarrays can allow for miniaturized multi-analyte, solid-phased immunoassay where many, and potentially thousands, of immobilized individual protein spots on a microscopic slide can be exposed to antibodies from a serum sample (e.g., taken from a dog), and identification of selective binding of the immobilized by antibodies from the serum sample detection of a label (e.g., fluorescent labeling) using an immunoassay (e.g., ELISA) reaction on the surface. The image processing and pattern recognition can be quantitatively analyzed. Protein microarrays include both analytical protein microarrays and functional protein microarrays. Functional protein microarrays typically involve spotting proteins and can be used for the characterization of protein functions, including protein-protein binding, biochemical activity, enzyme-substrate relationships, and immune responses (Poetz et al., 2005; Chen and Zhu, 2006). A variety of surface chemistry can be used to associate with or bind a polypeptide to the solid support. For example, the polypeptide can be covalently bonded to a solid support surface containing an aldehyde, epoxy, NHS, carboxylic ester, etc. A polypeptide may utilize adsorption to attach to a polyvinylidene fluoride (PVDF), nitrocellulose membrane, or polystyrene solid support. Diffusion can be used to associate the polypeptide with an agarose/polyacrylamide gel or hydrogel surface. Affinity capture can be used to attach a polypeptide to a Ni2+-NTA, streptavidin, or glutathione on a surface. In some instances, polypeptides can be associated with or attached to a metals surface such as gold, silver, or steel. These chemistries are further described in (Chen and Zhu, 2006). Fluorescent dyes with narrow excitation and emission spectra, such as Cy3, Cy5, and equivalents, are commonly used for detection because they are convenient and provide a wide linear detection range compared with other labeling systems (Hall et al., 2007). Moreover, these fluorescent dyes can provide a multicolor detection system, which can be utilized in multiplex assays.

Microarray signals may be detected by scanning the microarray with a variety of laser or CCD-based scanners, and extracting features with numerous software packages, for example, Imagene (Biodiscovery), Feature Extraction Software (Agilent), Scanalyze (Eisen, M. 1999. SCANALYZE User Manual; Stanford Univ., Stanford, Calif. Ver 2.32.), GenePix (Axon Instruments).

High-throughput protein systems include commercially available systems from Ciphergen Biosystems, Inc. (Fremont, Calif.) such as Protein Chip® arrays and the Schleicher and Schuell protein microspot array (FastQuant Human Chemokine, S&S Bioscences Inc., Keene, NH, US). In one embodiment, the high-throughput protein assay system may be the Bio-CD system using the SDI™ (Spinning Disc Interferometry) technology by Quadraspec, Inc. (West Lafayette, IN). Detailed discussions of the Bio-CD system are found in, e.g., U.S. Pat. Nos. 6,685,885, 7,405,831, 7,552,282, 7,659,968, 7,663,092, 7,787,126, 7,910,356, U.S. Pat. Pub. No. 2004/0166593, U.S. Pat. Pub. No. 2006/0256676, U.S. Pat. Pub. No. 2007/0023643, U.S. Pat. Pub. No. 2007/0212257, U.S. Pat. Pub. No. 2007/0259366, U.S. Pat. Pub. No. 2008/0175755, U.S. Pat. Pub. No. 2009/0002716, U.S. Pat. Pub. No. 2009/0263913 now U.S. Pat. No. 8,298,831, U.S. Pat. Pub. No. 2010/0145627 now U.S. Pat. No. 8,072,585, and Canadian Pat. Pub. No. 2681722, each of which is hereby incorporated in its entirety.

The parallel immunoassay results obtained as described above can then be used for diagnosis of the specific disorder. The individual proteins/antibodies can be detected or quantified by any of a number of means well known to those of skill in the art. In one aspect, a qualitative change in one or more proteins/antibodies is determined. Qualitative changes include the appearance of a proteins/antibodies spot that is not detectable in samples obtained from normal controls or the disappearance of a proteins/antibodies spot which is detectable in normal controls but not in the sample taken from an affected subject.

In another aspect, a quantitative change in one or more proteins/antibodies may be measured. The concentration of protein/antibody levels may be expressed in absolute terms, for example, optical density as read by image analysis. Alternatively, the concentrations can be expressed as a fraction, relative to normal levels of the same protein/antibody.

As used herein, a "sample" is any sample that comprises or is suspected to comprise antibodies. Preferably, the sample is whole blood, sputum, serum, plasma, saliva, cerebrospinal fluid or urine. The sample may be a blood, serum or plasma sample obtained from a subject or patient.

Accordingly, methods of identifying an *Ehrlichia* infection in a mammalian subject are provided herein. Such a method may involve contacting a sample from the subject with an isolated immunoreactive polypeptide disclosed comprising any one of SEQ ID NOs:1-7, in some preferred embodiments E177 (SEQ ID NO 1) and/or E208 (SEQ ID NO:7), under conditions that allow peptide-antibody complexes to form, and detecting the peptide-antibody complexes. In these embodiments, the detection of the peptide-antibody complexes is an indication that the subject has an *Ehrlichia* infection. The *Ehrlichia* organism may be an *E. chaffeensis* organism or an *E. canis* organism. The subject may be a human or a dog. As with other methods disclosed herein, the detection step may be accomplished using any appropriate type of assay known in the art, such as a lateral flow assay or an ELISA.

The terms "subject" and "patient" are used interchangeably herein, and may refer to a mammal, especially a human or a dog. In certain embodiments, a "subject" or "patient" refers to a mammalian *Ehrlichia* host (i.e., animal infected with an *Ehrlichia* organism). An *Ehrlichia* host may be, for example, human or non-human primate, bovine, canine, caprine, cavine, corvine, epine, equine, feline, hircine, lapine, leporine, lupine, murine, ovine, porcine, racine, vulpine, and the like, including livestock, zoological specimens, exotics, as well as companion animals, pets, and any animal under the care of a veterinary practitioner. A subject may be or may not be infected with an *Ehrlichia* organism, and a subject may be a mammal suspected of being infected with an *Ehrlichia* organism.

A. ELISA

In certain embodiments, the detection of a peptide-antibody complex described herein is accomplished using an enzyme linked immunosorbent assay (ELISA). This assay may be performed by first contacting an immunoreactive polypeptide (e.g., a polypeptide comprising any one of SEQ ID NOs:1-7, in some preferred embodiments E177 (SEQ ID NO 1) and/or E208 (SEQ ID NO:7)) that has been immobilized on a solid support, commonly the well of a microtiter plate, with the sample, such that antibodies specific for the peptide within the sample are allowed to bind to the immobilized peptide. Unbound sample is then removed from the immobilized peptide and a detection reagent capable of binding to the immobilized antibody-polypeptide complex is added. The amount of detection reagent that remains bound to the solid support is then determined using a method appropriate for the specific detection reagent.

In some embodiments, the detection reagent contains a binding agent (such as, for example, Protein A, Protein G, immunoglobulin, lectin or free antigen) conjugated or covalently attached to a reporter group or label. Exemplary reporter groups or labels include enzymes (such as horseradish peroxidase), substrates, cofactors, inhibitors, dyes, radionuclides, luminescent groups, fluorescent groups and biotin. The conjugation of binding agent to reporter group or label may be achieved using standard methods known to those of ordinary skill in the art. Common binding agents may also be purchased conjugated to a variety of reporter groups from many commercial sources (e.g., Zymed Laboratories, San Francisco, CA; and Pierce, Rockford, IL.).

In an aspect of the present disclosure, the presence or absence of *Ehrlichia* specific antibodies may be determined in the sample by comparing the level of a signal detected from a reporter group or label in the sample with the level of a signal that corresponds to a control sample or predetermined cut-off value. In certain embodiments, the cut-off value may be the average mean signal obtained when the immobilized ehrlichial immunoreactive peptide is incubated with samples from an uninfected subject. The cut-off value may be determined using a statistical method or computer program.

B. Lateral Flow Tests

Lateral flow tests may also be referred to as immunochromatographic strip (ICS) tests or simply strip-tests. In general, a lateral flow test is a form of assay in which the test sample flows laterally along a solid substrate via capillary action, or alternatively, under fluidic control. Such tests are often inexpensive, require a very small amount (e.g., one drop) of sample, and can typically be performed reproducibly with minimal training. The economical simplicity and robustness of many lateral flow assay formats makes these types of tests ideal for identifying an *Ehrlichia* (e.g., *E. chaffeensis* or *E. canis*) infection at the point of care, which can be particularly important when the subject is, for example, a human or dog exhibiting detectable antibodies during the treatable acute phase of infection.

Exemplary lateral flow device formats include, but are not limited to, a dipstick, a card, a chip, a microslide, and a cassette, and it is widely demonstrated in the art that the choice of format is largely dependent upon the features of a particular assay. Accordingly, lateral flow devices are now ubiquitous in human and veterinarian medicine and quite varied, providing many options to the ordinarily skilled artisan for detecting a peptide-antibody complex in a sample using a lateral flow assay (See any of U.S. Pat. Nos. 7,344,893, 7,371,582, 6,136,610, and U.S. Patent Applications, 2005/0250141 and 2005/0047972 now U.S. Pat. No. 7,722,817, or Koczula et al. (2016) each incorporated herein by reference.) By way of a nonlimiting example, a sample from a subject suspected of having an *Ehrlichia* infection is applied to a lateral flow device comprising at least a sample zone and a binding zone. The sample may be a serum sample that may be drawn laterally from the sample zone to the binding zone which comprises an immunoreactive polypeptide disclosed herein (e.g., a polypeptide comprising any one of SEQ ID NOs:1-7, such as E177 (SEQ ID NO 1) and/or E208 (SEQ ID NO:7)) immobilized to a surface of the lateral flow device. In this example, the binding of the immobilized ehrlichial immunoreactive polypeptide on the lateral flow device is an indication that *Ehrlichia* specific antibodies are present in the sample from the subject, indicating an *Ehrlichia* infection in the subject, such as an *E. chaffeensis* infection in the subject.

In related embodiments, an ELISA assay as described above may be performed in a rapid flow-through, lateral flow, or strip test format, wherein the antigen is immobilized on a membrane, such as a nitrocellulose membrane. In this flow-through test, *Ehrlichia* antibodies within the sample bind to the immobilized ehrlichial immunoreactive peptide as the sample passes through the membrane. A detection reagent, such as protein A labeled with gold, a fluorophore, or a chromophore, binds to the peptide-antibody complex as the solution containing the detection reagent flows through the membrane. Peptide-antibody complexes bound to detection reagent may then be detected, as appropriate for the detection reagent used (e.g., based on the presence or absence of a visibly detectable color or fluorescent label, a nanoparticle, a luminescent rare earth nanoparticle, a luminous nanoparticle, a strontium aluminate nanoparticle (e.g., see Paterson et al., 2014; and Wang et al., 2017, etc.).

In an aspect, a flow-through format ELISA may be performed in which one end of the membrane to which a polypeptide comprising any one of SEQ ID NOs:1-7, such as E177 (SEQ ID NO 1) and/or E208 (SEQ ID NO:7), is immobilized may be immersed in a solution containing the sample, or the sample may be added to an area (i.e., a sample zone) at one end of the membrane. The sample migrates along the membrane through a region (i.e., a labeling zone) comprising the detection reagent, and flows to the area (i.e., a binding zone) comprising the immobilized immunoreactive peptide. An accumulation of detection reagent at the binding zone indicates the presence of *Ehrlichia* specific antibodies in the sample.

Typically, a flow-through ELISA may feature a detection reagent applied to a test strip in a pattern, such as a line, that can be read visually. As with other lateral flow tests, the absence of such a pattern typically indicates a negative result. It is within the ability of an ordinarily skilled artisan to select an amount of the immunoreactive polypeptide for immobilization on the membrane that can generate a visually discernible pattern when the biological sample contains a level of antibodies that would be sufficient to generate a positive signal in a standard format ELISA. The amount of peptide immobilized on the membrane may range from about 25 ng to about 1 mg.

C. Particulate-Based Assays

In general, particle-based assays use a capture-binding partner, such as an antibody or an antigen in the case of an immunoassay, coated on the surface of particles, such as microbeads, crystals, chips, or nanoparticles. Particle-based assays may be effectively multi-plexed or modified to assay numerous variables of interest by incorporating fluorescently labeled particles or particles of different sizes in a single assay, each coated or conjugated to one or more labeled capture-binding partners. The use of sensitive detection and amplification technologies with particle-based assay platforms known in the art has resulted in numerous flexible and sensitive assay systems to choose from in performing a method described herein. For example, a multiplex particle-based assay such as the suspension array Bio-Plex® assay system available from Bio-Rad Laboratories, Inc. (Hercules, CA) and Luminex, Inc. (Austin, TX) may be useful in identifying *Ehrlichia* antibodies in a sample.

In an aspect, the present disclosure contemplates the immobilization of an isolated immunoreactive polypeptide (e.g., a polypeptide comprising any one of SEQ ID NOs:1-7, E177 (SEQ ID NO 1) and/or E208 (SEQ ID NO:7)) on a surface of a particle for use in a particle-based immunoassay. As described herein, methods of peptide immobilization onto support surfaces is well known in the art. In a preferred embodiment, a labeled her immunoreactive polypeptide disclosed herein is immobilized onto a surface of a particle and the peptide-particle complex is employed in an ELISA or in a flow cytometry assay according to established protocols.

VI. Vectors

Vectors encoding an engineered immunoreactive polypeptide comprising any one of any one of SEQ ID NOs:1-7, such as E177 (SEQ ID NO 1) and/or E208 (SEQ ID NO:7), are provided. The polynucleotide may be codon-optimized for expression in a non-human organism (e.g., a bacterium, a yeast cell, an insect cell and a mammalian cell). In some embodiments, the polynucleotide is DNA or RNA.

An expression vector comprising cDNA encoding a polypeptide or a target molecule is introduced into *Escherichia coli*, yeast, an insect cell, an animal cell or the like for expression to obtain the polypeptide. Polypeptides used in the present invention can be produced, for example, by expressing a DNA encoding it in a host cell using a variety of methods. A recombinant vector is produced by inserting a cDNA downstream of a promoter in an appropriate expression vector. The vector is then introduced into a host cell suitable for the expression vector. The host cell can be any cell so long as it can express the gene of interest, and includes bacteria (e.g., *Escherichia coli*), an animal cell and the like. Expression vector can replicate autonomously in the host cell to be used or vectors which can be integrated into a chromosome comprising an appropriate promoter at such a position that the DNA encoding the polypeptide can be transcribed.

Silent modifications can be made to the nucleic acids that do not alter, substitute or delete the respective amino acid in the recombinant protein. Such modification may be necessary to optimize, for example, the codon usage for a specific recombinant host. The nucleotide sequences can be modified to replace codons that are considered rare or have a low frequency of appropriate t-RNA molecules to a more suitable codon appropriate for the expression host. Such codon tables are known to exist and are readily available to one skilled in the art. In addition, silent modification can be

VII. Ehrlichia Vaccine and Immunogenic Compositions

Previous work has shown that Ehrlichial proteins that induce antibody responses can provide protective immune responses. It is anticipated that an immunoreactive protein provided herein (e.g., a polypeptide comprising any one of SEQ ID NOs:1-7, in some preferred embodiments E177 (SEQ ID NO 1) and/or E208 (SEQ ID NO:7)) may be included in a pharmaceutical composition such as a vaccine composition for administration to a mammalian or human subject. For example, protection against *E. chaffeensis* infection has been demonstrated with epitope-specific antibodies directed at OMP and TRPs in in vitro models and in animal models (Kuriakose et al., 2012; Li et al., 2002; Li et al., 2001), demonstrating that proteins that elicit strong antibody responses to linear epitopes are protective.

In select embodiments, it is contemplated that an ehrlichial immunoreactive polypeptide comprising any one of SEQ ID NOs:1-7, such as E177 (SEQ ID NO 1) and/or E208 (SEQ ID NO:7), may be included in a vaccine composition and administered to a subject (e.g., a human or dog) to induce an immune response in the subject that may substantially prevent or ameliorate infection in the subject by an *Ehrlichia* organism such as *Ehrlichia chaffeensis* or *Ehrlichia canis*. A vaccine composition for pharmaceutical use in a subject may comprise an immunoreactive polypeptide comprising any one of SEQ ID NOs:1-7, E177 (SEQ ID NO 1) and/or E208 (SEQ ID NO:7), and a pharmaceutically acceptable carrier.

The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1289-1329, 1990, incorporated herein by reference). Except insofar as any conventional carrier is incompatible with the active ingredient, its use in the vaccine compositions of the present disclosure is contemplated.

As used herein, a "protective immune response" refers to a response by the immune system of a mammalian host to an *Ehrlichia* antigen which results in increased recognition of the antigen and antibody production by the immune system of the mammalian host upon subsequent exposure to an *Ehrlichia* pathogen. A protective immune response may substantially reduce or prevent symptoms as a result of a subsequent exposure to *Ehrlichia chaffeensis* or *Ehrlichia canis*.

In some embodiments, a vaccine composition of the present disclosure may comprise an immunoreactive polypeptide (e.g., having a sequence that has at least about 90%, 91%, 92%, 93%, 94%, 95%, 96%, 97%, 98%, 99%, or 100% sequence identity to any one of SEQ ID NOs:1-7). In some embodiments, a vaccine composition comprising the immunoreactive polypeptide may be used to induce a protective immune response against *Ehrlichia chaffeensis* (e.g., in a human or dog subject).

A person having ordinary skill in the medical arts will appreciate that the actual dosage amount of a vaccine composition administered to an animal or human patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, vaccine compositions may comprise, for example, at least about 0.1% of the immunoreactive polypeptide. In other embodiments, the active compound may comprise between about 2% to about 75% of the weight of the unit, or between about 25% to about 60%, for example, and any range derivable therein. As with many vaccine compositions, frequency of administration, as well as dosage, will vary among members of a population of animals or humans in ways that are predictable by one skilled in the art of immunology. By way of nonlimiting example, the pharmaceutical compositions and vaccines may be administered by injection (e.g., intracutaneous, intramuscular, intravenous or subcutaneous), intranasally (e.g., by aspiration) or orally. Between 1 and 3 doses may be administered over a 1-36 week period. In some embodiments, 3 doses are administered, at intervals of 3-4 months, and booster vaccinations may be given periodically thereafter.

In some embodiments, a "suitable dose" is an amount of an immunoreactive polypeptide that, when administered as described above, is capable of raising an immune response in an immunized patient sufficient to protect the subject from an *Ehrlichia* infection in subsequent exposures to *Ehrlichia* organisms. In general, the amount of polypeptide present in a suitable dose (or produced in situ by the nucleic acid in a dose) may range from about 1 pg to about 500 mg per kg of host, typically from about 10 pg to about 10 mg, preferably from about 100 pg to about 1 mg and more preferably from about 100 pg to about 100 microgram.

A vaccine composition of the present disclosure may comprise different types of carriers depending on whether it is to be administered in solid, liquid or aerosol form, and whether it needs to be sterile for such routes of administration as injection. A vaccine composition disclosed herein can be administered intramuscularly, intradermally, subcutaneously, intravenously, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subconjunctivally, intravesicularly, mucosally, intrapericardially, locally, orally, intranasally, or by inhalation, injection, infusion, continuous infusion, lavage, or localized perfusion. A vaccine composition may also be administered to a subject via a catheter, in cremes, in lipid compositions, by ballistic particulate delivery, or by other method or any combination of the forgoing as would be known to one of ordinary skill in the art (see, for example, Remington: The Science and Practice of Pharmacy, 21$^{st}$ Ed. Lippincott Williams and Wilkins, 2005, incorporated herein by reference).

Any of a variety of adjuvants may be employed in in a vaccine provided herein to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bordatella pertussis* or *Mycobacterium tuberculosis*. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

Sterile injectable solutions are prepared by incorporating the active peptides in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

In some embodiments, an immunogenic or vaccine composition as disclosed herein comprises an *Ehrlichia* bacterin, such as an *E. Canis* bacterin or an *E. chaffeensis* bacterin. E *Canis* bacterin may be prepared by heat-inactivating or chemically-inactivating the *Ehrlichia* bacteria. A variety of methods may be used to generate an *E. chaffeensis* or E. *Canis* bacterin. For example, the bacteria may be inactivated by heat or psoralen in the presence of ultraviolet light to produce the bacterin. Additional methods that may be used to generate an *Ehrlichia* or E. *Canis* bacterin include those described, e.g., in WO2005087803, EP2433646, Vega et al., 2007; or Stuen et al., 2015.

A variety of adjuvants are known that can be included. For example, adjuvants such as MF59, AS01, AS02, AS03, AS04, Virosomes, CAF01, CAF04, CAF05, Montanide ISA™ 720, or Montanide ISA™ 51 (e.g., Bonam et al., 2017) can be used in some embodiments.

The adjuvant may be a liposome or emulsion formulation. The liposomes may be unilamellar, multilamellar, or multivesicular. In some embodiments, the immunogenic or vaccine composition comprises a lipid or lipid-containing adjuvant. In some embodiments, the liposomes are cationic liposomes. In various embodiments, adjuvants such as MF59 (e.g., Calabro et al., 2013), AS01 (Didierlaurent, et al., 2014), AS02 (Gargon and Van Mechelen, 2011), AS03 (Morel et al., 2011), AS04 (Didierlaurent et al., 2009), Virosomes (Künzi et al., 2009), CAF01 (Tandrup Schmidt et al., 2016), CAF04 (Billeskov et al., 2016), CAF05 (Billeskov et al., 2016), Montanide ISA™ 720 (Aucouturier et al., 2002), or Montanide ISA™ 51 (Aucouturier et al., 2002).

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

VIII. *Ehrlichia* Detection and Vaccination Kits

A polypeptide comprising any one of SEQ ID NOs:1-7, in some preferred embodiments E177 (SEQ ID NO 1) and/or E208 (SEQ ID NO:7), can be included in a kit for the diagnosis or identification of coinfections with a single or multiple *Ehrlichia* spp. and exposure or infection in a subject. The kit may be used to determine whether a subject has been immunized against *Ehrlichia* or is actively infected with an *Ehrlichia* organism.

The kit can be used for detecting *Ehrlichia* spp. antibodies in a sample, to identify an *Ehrlichia* exposed individual (e.g., a human or dog), for determining whether a subject has been immunized against *Ehrlichia* or is actively infected with an *Ehrlichia* organism, or for vaccinating a subject against an *Ehrlichia* organism. In these embodiments, one or more immunoreactive polypeptide comprising any one of SEQ ID NOs:1-7, E177 (SEQ ID NO 1) and/or E208 (SEQ ID NO:7), may be comprised in the kit. The immunoreactive polypeptide in the kit may be detectably labeled or immobilized on a surface of a support substrate also comprised in the kit. The immunoreactive polypeptide(s) may, for example, be provided in the kit in a suitable form, such as sterile, lyophilized, or both.

The support substrate comprised in a kit of the invention may be selected based on the method to be performed. By way of nonlimiting example, a support substrate may be a multi-well plate or microplate, a membrane, a filter, a paper, an emulsion, a bead, a microbead, a microsphere, a nanobead, a nanosphere, a nanoparticle, an ethosome, a liposome, a niosome, a transferosome, a dipstick, a card, a celluloid strip, a glass slide, a microslide, a biosensor, a lateral flow apparatus, a microchip, a comb, a silica particle, a magnetic particle, or a self-assembling monolayer.

As appropriate to the method being performed, a kit may further comprise one or more apparatuses for delivery of a composition to a subject or for otherwise handling a composition of the invention. By way of nonlimiting example, a kit may include an apparatus that is a syringe, an eye dropper, a ballistic particle applicator (e.g., applicators disclosed in U.S. Pat. Nos. 5,797,898, 5,770,219 and 5,783, 208, and U.S. Patent Application 2005/0065463 now U.S. Pat. No. 8,353,861), a scoopula, a microslide cover, a test strip holder or cover, and such like.

A detection reagent for labeling a component of the kit may optionally be comprised in a kit for performing a method of the present disclosure. In particular embodiments, the labeling or detection reagent is selected from a group comprising reagents used commonly in the art and including, without limitation, radioactive elements, enzymes, molecules which absorb light in the UV range, and fluorophores such as fluorescein, rhodamine, auramine, Texas Red, AMCA blue and Lucifer Yellow. In other embodiments, a kit is provided comprising one or more container means and a BST protein agent already labeled with a detection reagent selected from a group comprising a radioactive element, an enzyme, a molecule which absorbs light in the UV range, and a fluorophore.

The kit may be used for detecting anti-*Ehrlichia* antibodies in a sample, which may be used for identification of an *Ehrlichia* infection in a subject, and/or for determining whether a subject has been immunized against *Ehrlichia* or is actively infected with an *Ehrlichia* organism. Such a kit may comprise one or more immunoreactive polypeptides (e.g., a polypeptide comprising any one of SEQ ID NOs:1-7, E177 (SEQ ID NO 1) and/or E208 (SEQ ID NO:7)), and the peptides may be detectably labeled and immobilized to one or more support substrates comprised in the kit.

The kit preferably comprises an immunoreactive polypeptide comprising any one of SEQ ID NOs:1-7, such as E177 (SEQ ID NO 1) and/or E208 (SEQ ID NO:7). The polypeptides may be immobilized to one or more separate lateral flow assay devices, such as a nitrocellulose test strip. In these embodiments, each of the test strips may further comprise a detection reagent, for example, a chromophore-labeled protein A. Such a kit may further comprise one or more containers for sample material, one or more diluents for sample dilution, and one or more control indicator strips for comparison.

When reagents and/or components in a kit are provided in a lyophilized form (lyophilisate) or as a dry powder, the lyophilisate or powder can be reconstituted by the addition of a suitable solvent. The solvent may be a sterile, pharmaceutically acceptable buffer and/or other diluent. The solvent may also be provided as part of a kit.

When the components of a kit are provided in one and/or more liquid solutions, the liquid solution may be, by way of non-limiting example, a sterile, aqueous solution. The compositions may also be formulated into an administrative composition. In this case, the container means may itself be a syringe, pipette, topical applicator or the like, from which the formulation may be applied to an affected area of the body, injected into a subject, and/or applied to or mixed with the other components of the kit.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Engineered Immunoreactive Polypeptides

A nucleic acid encoding the non-natural polypeptide E177 (SEQ ID NO:1) was synthesized, and E177 polypeptide was produced and purified, as follows. The vector pET-14b with cutting sites NdeI/BamHI and with a stop codon in insert was used for experiments. E177 was expressed in Lemo21 (DE3) competent *E. coli* cells, and E177 polypeptide was purified with His60 Ni Superflow Resin. The expected molecular weight of 22KD was observed for the E177 synthetic polypeptide.

Protein Expression Using Lemo21(DE3) (C2528) was performed (New England BioLabs; Ipswich, MA), as follows. Transformed expression plasmid into Lemo21(DE3). Transformation plates containing antibiotic to select the expression plasmid and 30 g/ml chloramphenicol to maintain pLemo, a pACYC184 derivative with a p15A origin of replication. Incubated overnight at 37° C. Resuspended a single colony in a 1 or 2 ml liquid culture with both antibiotics and grown overnight to produce a starter culture. Used media without glucose for optimal strain performance. To sample different expression levels, 10 ml expression cultures were produced at the beginning of day 2 with various levels of L-rhamnose (e.g., 0,100,250, 500, 750, 1,000 and 2,000 μM) for difficult targets. Inoculated expression culture with 0.2 ml of starter culture. Incubated at 37° C. until OD600 reaches 0.4-0.8. Induced with 40 μl of a 100 mM stock of IPTG (final concentration of 400 μM). Induced for ~5 hours to overnight at 30 or 37° C. Checked for expression either by Coomassie stained protein gel, Western Blot or activity assay. Checked expression in both the total cell extract (soluble+insoluble) and the soluble fraction only.

Detection of *E. canis* and *E. chaffeensis* antibodies by ELISA. Sera from dogs (n=55) suspected of infection with *Ehrlichia* spp. were tested for reactivity with antigens E177 (SEQ ID NO:1) and E208 (SEQ ID NO:7), and this reactivity was compared with reactivity of the serum samples for synthetically produced immunoreactive polypeptides found in *E. canis* protein TRP36 having the sequence: TEDSVSAPATEDSVSAPATEDSVSAPA (referred to as "Crtl peptide 1"; SEQ ID NO:8). The *E. canis* protein TRP36 is highly immunoreactive in serum samples from dogs exposed to *Ehrlichia*, and this assay was used as a high stringency test to evaluate the sensitivity and specificity of the engineered E177 and E208 polypeptides against highly immunoreactive polypeptides found in naturally-occurring *E. canis* pathogens. Results are shown in FIGS. 1-3. The control peptide 1 (SEQ ID NO:8) was chosen since this peptide is currently used as the standard of care for diagnosing ehrlichiosis in dogs.

Performance of E177 in detecting of *E. canis* antibodies in sera from 55 dogs suspected of canine monocytic ehrlichiosis (CME) by ELISA is shown in FIG. 1 and FIG. 2. E177 demonstrated overall stronger ELISA reactivity with *E. canis* antibodies compared to control peptide #1 in all positive sera (100%) tested. Increased analytical sensitivity of E177 was observed compared control peptide #1 in 22/40 (55%) positive dog sera that could contribute to improved laboratory and clinical diagnosis, earlier treatment, and improved disease outcome. Background from a pooled negative dog sera (n=10) was subtracted to obtain OD values for positive sera. Cutoff threshold OD>0.01 for positive.

Mean reactivity of E177 and control peptide with dog sera containing high (ELISA OD>1.0) and low (ELISA OD<1.0) *E. canis* antibodies levels was observed. Results are shown in FIG. 3.

Engineered polypeptides displayed significant immunoreactivity and advantages over the current standard of care (SEQ ID NO:7). Even compared this highly immunoreactive polypeptide found in naturally occurring proteins from *E. canis*, the engineered E177 displayed an increased immunoreactivity, and E177 detected *Ehrlichia* infection in multiple individuals where the highly immunoreactive control peptide did not detect immunoreactivity (see, e.g., results in FIG. 1 from subjects 2, 3, 4, 9, 11, 21, 22, 23, 32, 33, 37, 44, 54). When the immunoreactivity against E177 was compared with the immunoreactivity of control peptide #1, a significant increase was observed (FIG. 2). The engineered polypeptide E208 was immunoreactive against sera from multiple samples (FIG. 3), and stronger immunoreactivity as compared to E177 was observed in several serum samples (e.g., see samples from subjects 12 and 53), and E208 reacted with antibodies against *Ehrlichia* in multiple serum samples that were not detected by the control peptide (see for examples results from subjects 2, 3, 4, 7, 12, 15, 16, 19, 20, 21, 22, 29, 31, 46, 47, 52, 53, 54, 55) indicating specific reactivity with *E. chaffeensis* exposed samples. Immunoreactivity of both engineered polypeptides (E177 and E208) in some serum samples (e.g., 5, 6, 17, 41) but not in other serum samples (e.g., 44, 38, 31, 34) demonstrates the ability of the engineered polypeptides to detect coinfections in addition to discriminating between antibodies from distinct *Ehrlichia* spp. These results demonstrate that engineered polypeptides E177 and E208 are highly sensitive and specific diagnostic antigens that display advantages over the current diagnostic "gold standard" of TRP36 ("Ctrl peptide 1").

ELISA plates (Nunc, MaxiSorp) were coated with 50 l/well of E177/E208 (100 ng/well) or synthetic peptide (1 ug/well) diluted in PBS. Plates were incubated overnight at 4° C., or 1 h at RT on a plate shaker (300 rpm) for antigen coating. Plates were washed three times with 200 µl of TBST (TBS with 0.2% Tween-20) on a plate washer and blocked using blocking buffer (5% normal goat serum in TBST) and incubated at RT for 1 h with shaking. Plates were washed and dog sera (diluted 1:200) were added (50 µl/well) diluted in blocking buffer and incubate at RT for 1 h with shaking. Plates were washed 3 times and secondary goat anti-dog alkaline phosphatase-conjugate diluted in blocking buffer was added and incubated at RT for 1 h with shaking. Plates were washed 3 times and antibody binding visualized with BluePhos Phosphatase Substrate Solution A+B incubated at RT for 30 min with shaking in dark. ELISA $OD_{650}$ values were measured using a Molecular Devices iD5 plate reader. Results are shown in FIG. 1.

Detection of *Ehrlichia* spp. antibodies in dog sera. Sera with high *Ehrlichia* antibody titers as defined by ELISA OD values>1.0 were detected by most proteins/peptides. Lower ELISA OD values were observed against peptides compared to antigens E177/208 (FIG. 1). Dog sera with lower antibody levels (<1.0 ELISA OD) reacted with E208/E177 more strongly and consistently with antibodies in dog sera compared with positive control peptides.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,087,112
U.S. Pat. No. 7,663,092
U.S. Pat. No. 4,220,450
U.S. Pat. No. 4,373,932
U.S. Pat. No. 4,472,509
U.S. Pat. No. 4,897,268
U.S. Pat. No. 4,938,948
U.S. Pat. No. 5,075,109
U.S. Pat. No. 5,143,854
U.S. Pat. No. 5,215,882
U.S. Pat. No. 5,440,013
U.S. Pat. No. 5,446,128
U.S. Pat. No. 5,470,723
U.S. Pat. No. 5,470,932
U.S. Pat. No. 5,543,504
U.S. Pat. No. 5,552,157
U.S. Pat. No. 5,565,213
U.S. Pat. No. 5,567,434
U.S. Pat. No. 5,618,914
U.S. Pat. No. 5,656,016
U.S. Pat. No. 5,670,155
U.S. Pat. No. 5,697,899
U.S. Pat. No. 5,707,807
U.S. Pat. No. 5,738,868
U.S. Pat. No. 5,741,516
U.S. Pat. No. 5,770,219
U.S. Pat. No. 5,779,708
U.S. Pat. No. 5,783,208
U.S. Pat. No. 5,795,587
U.S. Pat. No. 5,797,898
U.S. Pat. No. 5,807,522
U.S. Pat. No. 5,837,832
U.S. Pat. No. 5,840,833
U.S. Pat. No. 5,853,744
U.S. Pat. No. 5,859,184
U.S. Pat. No. 5,891,506
U.S. Pat. No. 5,929,237
U.S. Pat. No. 5,958,342
U.S. Pat. No. 5,994,076
U.S. Pat. No. 6,004,755
U.S. Pat. No. 6,040,138
U.S. Pat. No. 6,048,695
U.S. Pat. No. 6,060,240
U.S. Pat. No. 6,090,556
U.S. Pat. No. 6,136,610
U.S. Pat. No. 6,210,708
U.S. Pat. No. 6,372,445
U.S. Pat. No. 6,617,142
U.S. Pat. No. 6,685,885
U.S. Pat. No. 6,875,750
U.S. Pat. No. 6,951,765
U.S. Pat. No. 7,163,677
U.S. Pat. No. 7,282,194
U.S. Pat. No. 7,344,893
U.S. Pat. No. 7,371,582
U.S. Pat. No. 7,405,831
U.S. Pat. No. 7,552,282
U.S. Pat. No. 7,659,968
U.S. Pat. No. 7,787,126
U.S. Pat. No. 7,910,356
U.S. Pat. No. 8,580,280
U.S. Pat. No. 8,980,288
U.S. Pat. No. 8,980,288
U.S. Pat. No. 9,545,439
U.S. Pat. No. 9,545,439
U.S. Pat. No. 9,662,385.
U.S. Pat. No. 10,117,921
U.S. Pat. No. 10,117,921
U.S. Pat. No. 10,117,921
U.S. Pat. No. 10,238,736
U.S. Patent Appln. 2004/0166593
U.S. Patent Appln. 2005/0047972
U.S. Patent Appln. 2005/0065463
U.S. Patent Appln. 2005/0250141
U.S. Patent Appln. 2006/0256676
U.S. Patent Appln. 2007/0023643

U.S. Patent Appln. 2007/0212257
U.S. Patent Appln. 2007/0259366
U.S. Patent Appln. 2007/0264664
U.S. Patent Appln. 2008/0175755
U.S. Patent Appln. 2009/0002716
U.S. Patent Appln. 2009/0005535
U.S. Patent Appln. 2009/0263913
U.S. Patent Appln. 2010/0145627
U.S. Patent Appln. 2019/0008953
U.S. Patent Appln. 2019/0038737
CA2681722
EP2433646
WO2005087803
Aucouturier, et al., *Expert Rev. Vaccines*, 1, 111-118, 2002.
Billeskov, et al., *PLoS One* 11, e0161217, 2016.
Bonam et al., *Trends in Pharmacological Sciences*, 38(9): 771-778, 2017.
Calabro et al., *Vaccine*, 31: 3363-3369, 2013.
Cardenas et al., *Clin. Vacc. Immunol.* 14: 123-128, 2007.
Carpino et al., *Org. Proc. Res. Dev.*, 7(1)28-37, 2003.
Chen and Zhu, 2006.
Didierlaurent, et al., *J. Immunol.*, 183: 6186-6197, 2009.
Didierlaurent, et al., *J. Immunol.*, 193, 1920-1930, 2013.
Didierlaurent, et al., *J. Immunol.* 193, 1920-1930, 2014.
Dumler et al., *Clin. Infect. Dis.*, 45:S45-S51, 2007.
Eisen, M. 1999. SCANALYZE User Manual; Stanford Univ., Stanford, Calif. Ver 2.32.
Feng and Walker, *Infect. Immun.*, 72:966-971, 2004.
Gargon and Van Mechelen, *Expert Rev. Vaccines*, 10, 471-486, 2011.
Hall et al., 2007.
He et al., Vaxign: the first web-based vaccine design program for reverse vaccinology and applications for vaccine development. J Biomed Biotechnol 2010:297505, 2010.
Koczula et al., 2016.
Künzi, et al., *Vaccine*, 27, 3561-3567, 2009.
Kuriakose et al., *Ehrlichia chaffeensis* transcriptome in mammalian and arthropod hosts reveals differential gene expression and post transcriptional regulation. PLoS One 6:e24136, 2011.
Kuriakose et al., Molecular basis of antibody mediated immunity against *Ehrlichia chaffeensis* involves species-specific linear epitopes in tandem repeat proteins. Microbes Infect 14:1054-1063, 2012.
Li and Winslow, Survival, replication, and antibody susceptibility of *Ehrlichia chaffeensis* outside of host cells. InfectImmun 71:4229-4237, 2003.
Li et al., Antibodies highly effective in SCID mice during infection by the intracellular bacterium *Ehrlichia chaffeensis* are of picomolar affinity and exhibit preferential epitope and isotype utilization. JImmunol 169:1419-1425, 2002.
Li et al., Outer membrane protein-specific monoclonal antibodies protect SCID mice from fatal infection by the obligate intracellular bacterial pathogen *Ehrlichia chaffeensis*. JImmunol 166:1855-1862, 2001.
Mizuno et al., Chemistry. 23(58):14394-14409, Oct. 17 2017.
Morel, S. et al., *Vaccine*, 29, 2461-2473, 2011.
Paterson et al., Anal Chem. 86(19):9481-8, Oct. 7, 2014.
Pierce Immunotechnology Catalog and Handbook, at A12-A13, 1991.
Poetz et al., 2005.
Remington's Pharmaceutical Sciences, 18th Ed. Mack Printing Company, 1289-1329, 1990.
Stuen et al., *Acta Vet Scand.*, 57:40, 2015.
Tandrup Schmidt, et al., *Pharmaceutics*, 8, 7, 2016.
The Science and Practice of Pharmacy, 21$^{st}$ Ed. Lippincott Williams and Wilkins, 2005.
Vega et al., *Vaccine*, 25:519-525, 2007.
Wang et al., 2017.
Winslow et al., *Ann. NY Acad. Sci.*, 990:435-443, 2003.
Winslow et al., *Infect. Immun.*, 68:2187-2195, 2000.
Winslow et al., Infection of the laboratory mouse with the intracellular pathogen *Ehrlichia chaffeensis*. InfectImmun 66:3892-3899, 1998.
Yager et al., *Infect. Immun.*, 73:8009-8016, 2005.
Zemella et al., *Cell-Free Protein Synthesis: Pros and Cons of Prokaryotic and Eukaryotic Systems. Chembiochem.;* 16(17):2420-2431, 2015.

The invention claimed is:

1. An immunoreactive polypeptide comprising SEQ ID NO:1 or SEQ ID NO:7, or a polypeptide at least 90% identical thereto.

2. The immunoreactive polypeptide of claim 1, wherein the polypeptide comprises SEQ ID NO:2.

3. The immunoreactive polypeptide of claim 1, wherein the polypeptide comprises SEQ ID NO:7.

4. The immunoreactive polypeptide of claim 1, wherein the polypeptide is less than 500 amino acids in length.

5. The immunoreactive polypeptide of claim 1, wherein the polypeptide is comprised in a pharmaceutical preparation.

6. The immunoreactive polypeptide of claim 5, wherein the pharmaceutical preparation is formulated for parenteral, intravenous, subcutaneous, intranasal, sublingual, or intradermal administration.

7. The immunoreactive polypeptide of claim 1, wherein the polypeptide is attached to a solid support or comprised in a diagnostic kit.

8. The immunoreactive polypeptide of claim 7, wherein the solid support is glass or plastic.

9. The immunoreactive polypeptide of claim 7, wherein the solid support is comprised in a lateral flow assay, or microfluidic device.

10. The immunoreactive polypeptide of claim 7, wherein the solid support is a microarray or a protein chip.

11. The immunoreactive polypeptide of claim 1, wherein the polypeptide is covalently bound to an epitope tag or a fluorescent label.

12. The immunoreactive polypeptide of claim 11, wherein the epitope tag is ALFA-tag, V5-tag, Myc-tag, HA-tag, Spot-tag, T7-tag or NE-tag.

13. The immunoreactive polypeptide of claim 11, wherein the fluorescent label is a green fluorescent protein (GFP), red fluorescent protein (RFP), Halo, SNAP, or CLIP.

14. A pharmaceutical preparation comprising the polypeptide of claim 1 and a pharmaceutically acceptable excipient.

15. The pharmaceutical preparation of claim 1, wherein the pharmaceutically acceptable excipient comprises an adjuvant.

16. The pharmaceutical preparation of claim 15, wherein the adjuvant is an emulsion or liposomes, or wherein the adjuvant comprises a lipid.

17. The pharmaceutical preparation of claim 14, wherein the composition further comprises an *Ehrlichia* bacterin.

18. A nucleic acid encoding the polypeptide of claim 1.

19. The nucleic acid of claim 18, wherein the nucleic acid is a DNA segment.

20. The nucleic acid of claim 19, wherein the nucleic acid is comprised in an expression vector.

21. A method of detecting antibodies that specifically bind an *Ehrlichia* organism in a test sample, comprising: (a) contacting an isolated polypeptide of claim 1 to the test sample; (b) detecting the peptide-antibody complexes; wherein the detection of the peptide-antibody complexes is an indication that antibodies specific for an *Ehrlichia* organism are present in the test sample.

22. The method of claim 21, wherein the *Ehrlichia* organism is an *Ehrlichia chaffeensis* organism.

23. The method of claim 21, wherein the *Ehrlichia* organism is an *Ehrlichia canis* organism.

24. The method of claim 21, wherein the step of detecting comprises performing an enzyme-linked immunoassay, a radioimmunoassay, an immunoprecipitation, a fluorescence immunoassay, a chemiluminescent assay, an immunoblot assay, a lateral flow assay, a flow cytometry assay, a multiplex immunoassay, a mass spectrometry assay, or a particulate-based assay.

25. The method of claim 24, wherein the step of detecting comprises a lateral flow assay or an enzyme-linked immunoassay, wherein the enzyme-linked immunoassay is an ELISA.

26. The method of claim 21, wherein the step of detecting is performed on a protein microarray or a protein chip.

27. The method of claim 21, wherein the test sample is a blood, serum, or plasma sample.

28. The method of claim 27, wherein the test sample is obtained from a dog.

29. The method of claim 27, wherein the test sample is obtained from a human.

* * * * *